US008980820B2

(12) United States Patent
Deutsch et al.

(10) Patent No.: US 8,980,820 B2
(45) Date of Patent: Mar. 17, 2015

(54) FATTY ACID BINDING PROTEINS AS DRUG TARGETS FOR ENDOCANNABINOIDS

(75) Inventors: Dale Deutsch, Stony Brook, NY (US); Martin Kaczocha, Dix Hills, NY (US); Sherrye Glaser, Dix Hills, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 515 days.

(21) Appl. No.: 13/145,058

(22) PCT Filed: Jan. 19, 2010

(86) PCT No.: PCT/US2010/021431
§ 371 (c)(1),
(2), (4) Date: Mar. 12, 2012

(87) PCT Pub. No.: WO2010/083532
PCT Pub. Date: Jul. 22, 2010

(65) Prior Publication Data
US 2012/0165388 A1    Jun. 28, 2012

(51) Int. Cl.
*A01N 61/00*    (2006.01)
*A01N 37/18*    (2006.01)
*G01N 33/94*    (2006.01)

(52) U.S. Cl.
CPC .......... *G01N 33/948* (2013.01); *G01N 2500/02* (2013.01); *G01N 2500/04* (2013.01); *G01N 2500/10* (2013.01)
USPC .................... 514/1; 424/9; 424/9.1; 436/501; 514/2

(58) Field of Classification Search
USPC ........ 424/9.1, 9.2, 9; 435/6, 91.1, 91.31, 455, 435/458; 436/501; 514/1, 2, 44; 536/23.1, 536/24.5
See application file for complete search history.

(56) References Cited

U.S. PATENT DOCUMENTS

| 6,713,602 | B1 | 3/2004 | Buchardt et al. |
| 6,723,560 | B2 | 4/2004 | Richelson et al. |
| 2003/0154032 | A1 | 8/2003 | Pittman et al. |
| 2004/0048907 | A1 | 3/2004 | Aquila et al. |
| 2004/0214236 | A1 | 10/2004 | Brines et al. |
| 2007/0155712 | A1 | 7/2007 | Zahn et al. |
| 2009/0004668 | A1* | 1/2009 | Chen et al. ............ 435/6 |

FOREIGN PATENT DOCUMENTS

| WO | 00/59506 A1 | 10/2000 |
| WO | WO 02/44321 * | 6/2002 |
| WO | 03/043624 A1 | 5/2003 |

OTHER PUBLICATIONS

Lovinger, D.M., J. Mol. Neurosci., vol. 33, pp. 87-93 (2007).*
Doench et al., Genes and Development, vol. 18, No. 5, pp. 504-511 (2004).*
Holen et al., Nucleic Acids. Res., vol. 30, No. 8, pp. 1757-1766 (2002).*
Opalinska et al., Nature Rev., vol. 1, pp. 503-514 (2002).*
Peracchi et al., Rev. Med. Virol., vol. 14, pp. 47-64 (2004).*
Crooke, S., Ann. Rev. Medicine, vol. 55, pp. 61-95 (2004).*
Agrawal et al., Nolecular Med. Today, vol. 6, pp. 72-81 (2000).*
Chirila et al., Biomaterials, vol. 23, pp. 321-342 (2002).*
Jang et al., Expert Rev. Medical Devices, vol. 1, No. 1, pp. 127-138 (2004).*
Paroo et al., Trends in Biotech., vol. 22, No. 8, pp. 390-394 (2004).*
Furuhashi, M. et al., "Treatment of Diabetes and Atherosclerosis by inhibiting Fatty-Acids-Binding Protein aP2", Nature (2007), vol. 447:7147, pp. 959-967.
Lovinger, D.M. et al., "Endocannabinold Liberation from Neurons in Transsynaptic Signalling", J. Mol. Neurosci. (2007), vol. 33:1, pp. 87-93.
Owada, Y. et al., "Fatty Acid Binding Protein: Localization and Functional Significance in the Brain", Tohoku J. Exp. Med. (2008), vol. 214:3, pp. 213-220.
Veerkamp, J.H. et al., "Fatty Acid-Binding Proteins of Nervous Tissue", J. Mol. Neurosci. (2001), vol. 16:2-3, pp. 133-142.
Blankman, J.L. et al., "A Comprehensive Profile of Brain Enzymes that Hydrolyze the Endocannabinoid 2-Arachidonoylglycerol", Chemistry & Biology (2007), vol. 14, pp. 1347-1356.
Bojesen, I.N. et al., "Membrane transport of anandamide through resealed human red blood cell membranes", J. of Lipid Research (2005), vol. 46, pp. 1652-1659.
Bojesen, I.N. et al., "Effect of an unstirred layer on the membrane permeability of anandamide", J. of Lipid Research (2006), vol. 47, pp. 561-570.
Brummelkamp, T.R. et al., "A System for Stable Expression of Short Interfering RNAs in Mammalian Cells", Science (2002), vol. 296, pp. 550-553.

(Continued)

*Primary Examiner* — Jane Zara
(74) *Attorney, Agent, or Firm* — Kenyon & Kenyon LLP

(57) ABSTRACT

The invention provides a method of modulating the level of an endocannabinoid in a subject in need thereof comprising administering an effective amount of an agent that inhibits the interaction of the endocannabinoid with an intracellular fatty acid binding protein (FABP). The invention also provides a method of identifying an agent for modulating the level of an endocannabinoid in a subject comprising testing the agent for its ability to modulate binding of the endocannabinoid with an intracellular FABP. The invention also provides a method of identifying an agent for modulating the level of an endocannabinoid in a subject comprising testing the agent for its ability to modulate expression of an intracellular FABP. The invention also provides a method of identifying an agent for treatment of a neurological disorder comprising testing the agent for its ability to modulate the interaction of an endocannabinoid with an intracellular FABP. The invention also relates to modulation of levels of fatty acid amides for treatment or amelioration of diseases or disorders by modulating binding of the fatty acid amides to fatty acid binding proteins. In one embodiment, the fatty acid binding protein is one or more of FABP3, FABP5, and FABP7. In one embodiment, the level of an endocannabinoid is modulated.

18 Claims, 5 Drawing Sheets

(56) References Cited

OTHER PUBLICATIONS

Cravatt, B.F., et al., "Supersensitivity to anandamide and enhanced endogenous cannabinoid signaling in mice lacking fatty acid amide hydrolase", PNAS (2001), vol. 98:16, pp. 9371-9376.
Cravatt, B.F., et al., "Functional disassociation of the central and peripheral fatty acid amide signaling systems", PNAS (2004), vol. 101:29, pp. 10821-10826.
De Marchi, N. et al., "Endocannabinoid signalling in the blood of patients with schizophrenia" Lipid in Health and Disease (2003), vol. 2; 9 pgs.
Deutsch, D.G. et al., "The Cellular Uptake of Anandamide is Copuled to its Breakdown by Fatty-acid Amide Hydrolase", J. of Biological Chemistry (2001), vol. 276:10, pp. 6967-6973.
Fasia, L. et al., "Uptake and metabolism of [3H]anandamide by rabbit platelets Lack of transporter?", Eur. J. Biochem., (2003), vol. 270, pp. 3498-3506.
Fegley, D. et al., "Anandamide transport is independent of fatty-acid amide hydrolase activity and is blocked by the hydrolysis-resistant inhibitor AM1172", PNAS (2004), vol. 101:23, pp. 8756-8761.
Fezza, F. et al., "Characterization of biotin-anandamide, a novel tool for the visualization of anandamide accumulation", J. of Lipid Research (2008), vol. 49, pp. 1216-1223.
Furuhashi, M. et al., "Treatment of diabetes and atherosclerosis by inhibiting fatty-acid-binding protein aP2", Nature (2007), vol. 447, pp. 959-968.
Furuhashi, M. et al., "Fatty acid-binding proteins: role in metabolic diseases and potential as drug targets", Nature Review: Drug Discovery (2008), vol. 7, pp. 489-503.
Glaser, S.T. et al., "Evidence against the presence of an anandamide transporter", PNAS (2003), vol. 100:7, pp. 4269-4274.
Glaser, S.T. et al., "Ex Vivo Imaging of Fatty Acid Amide Hydrolase Activity and Its Inhibition in the Mouse Brain", JPET (2006), vol. 316:3, pp. 1088-1097.
Glatz, J.F.C. et al., "Diurnal Variation of Cytosolic Fatty Acid-binding Protein Content and of Palmitate Oxidation in Rat Liver and Heart", J. Biological Chemistry (1984), vol. 259:7, pp. 4295-4300.
Gobbi, G. et al., "Antidepressant-like activity and modulation of brain monoaminergic transmission by blockade of anandamide hydrolysis", PNAS (2005), vol. 102:51, pp. 18620-18625.
Herman, A. et al., "2-Arachidonoylglycerol (2-AG) Membrane Transport: History and Outlook", AAPS Journal (2006), vol. 8:2, pp. E409-E412.
Hillard, C.J. et al., "Studies of Anandamide Accumulation Inhibitors in Cerebellar Granule Neurons: Comparison to Inhibition of Fatty Acid Amide Hydrolase", J. Mol. Neurosci. (2007), vol. 33:1, pp. 18-24.
Hohjoh, H. "Enhancement of RNAi activity by improved siRNA duplexes", FEBS Letters (2004), vol. 557, pp. 193-198.
Houghten, R.A. "General method for the rapid solid-phase synthesis of large numbers of peptides: Specificity of antigen-antibody interaction at the level of individual amino acids", PNAS (1985), vol. 82, pp. 5131-5135.
Kaczocha, M. et al., "Anandamide Uptake Is Consistent with Rate-limited Diffusion and Is Regulated by the Degree of Its Hydrolysis by Fatty Acid Amide Hydrolase", J. Biological Chemistry (2006), vol. 281:14, pp. 9066-9075.
Kaczocha, M. et al., "Identification of intracellular carriers for the endocannabinoid anandamide", PNAS (2009), vol. 106:15, pp. 6375-6380.
Maurelli, S. et al., "Two novel classes of neuroactive fatty acid amides are substrates for mouse neuroblastoma 'anandamide amidohydrolase'", FEBS Letters (1995), vol. 377, pp. 82-86.
McFarland, M.J. et al., "A Role for Caveolae/Lipid Rafts in the Uptake and Recycling of the Endogenous Cannabinoid Anandamide", J. Biological Chemistry (2004), vol. 279:40, pp. 41991-41997.
Mechoulam, R. et al., "Toward an anandamide transporter", PNAS (2005), vol. 102:49, pp. 17541-17542.
Moore, S.A. et al., "Identification of a high-affinity binding site involved in the transport of endocannabinoids", PNAS (2005), vol. 102:49, pp. 17852-17857.
Morcos, P.A. et al., "Vivo-Morpholinos: A non-peptide transporter delivers Morpholinos into a wide array of mouse tissues", BioTechniques (2008), vol. 45, pp. 613-623.
Morrow, F.D. et al., "Quantitation of hepatic fatty acid-binding proteins by post-chromatographic ligand binding assay", J. of Lipid Research (1983), vol. 24, pp. 324-331.
Moulton, J.D. et al., "Gene Knockdowns in Adult Animals: PPMOs and Vivo-Morpholinos", Molecules (2009), vol. 14, pp. 1304-1323.
Muccioli, G.G. et al., "Identification of a Novel Endocannabinoid-Hydrolyzing Enzyme Expressed by Microglial Cells", J. Neurosci. (2007), vol. 27:11, pp. 2883-2889.
Oliveira, S. et al., "Targeted Delivery of siRNA", J. Biomed and Biotech. (2006), vol. 2006, pp. 1-9.
Sagar, D.R. et al., "Inhibition of fatty acid amide hydrolase produces PPAR-alpha-mediated analgesia in a rat model of inflammatory pain", Br. J. of Pharmacology (2008), vol. 155, pp. 1297-1306.
Schroeder, F. et al., "Sterol Carrier Protein-2: New roles in regulating lipid rafts and signaling", Biochim Biophys Acta (2007), vol. 1771:6, pp. 700-718.
Storch, J. et al., "The Emerging Functions and Mechanisms of Mammalian Fatty Acid—Binding Proteins", Annu. Rev. Nutr. (2008), vol. 28, pp. 73-95.
Sulsky, R. et al., "Potent and selective biphenyl azole inhibitors of adipocyte fatty acid binding protein (aFABP)", Bioorg. Med. Chem. Letters (2007), vol. 17, pp. 3511-3515.
Thors, L. et al. "Inhibition of the cellular uptake of anandamide by genistein and its analogue daidzein in cells with different levels of fatty acid amide hydrolase-driven uptake", Br. J. Pharma. (2007), vol. 152, pp. 744-750.
Ui-Tei, K. et al., "Guidelines for the selection of highly effective siRNA sequences for mammalian and chick RNA interference", NAR (2004), vol. 32:3, pp. 936-948.
Wise, L.E. et al., "Evaluation of fatty acid amides in the carrageenan-induced paw edema model", NeuroPharma. (2008), vol. 54:1, pp. 181-188.
Yuan, B. et al., "siRNA Selection Server: an automated siRNA oligonucleotide prediction server", NAR (2004), vol. 32 (Web Server issue), pp. W130-W134.

* cited by examiner

FATTY ACID BINDING PROTEINS AS DRUG TARGETS FOR ENDOCANNABINOIDS

STATEMENT OF INTEREST

This invention was made with government support under DA016419 awarded by the National Institutes of Health. The government has certain rights in the invention.

CROSS-REFERENCE TO RELATED APPLICATIONS

This application claims priority to U.S. Application No. 61/145,737, filed Jan. 19, 2009 and U.S. Application No. 61/158,897, filed Mar. 10, 2009, which are incorporated herein by reference in their entireties.

FIELD OF THE INVENTION

The present invention relates to methods of modulating the levels of endocannabinoids in a subject by administering an agent that modulates the interaction of the endocannabinoids with intracellular fatty acid binding proteins. The invention further provides methods of identifying agents that modulates endocannabinoid function by contacting a test agent with a fatty acid binding protein (FABP) expressed in the CNS, and detecting endocannabinoid binding to the FABP. The agent is then identified by its ability to modulate endocannabinoid binding to the FABP relative to binding of the endocannabinoid to the FABP in the absence of the agent. The invention further provides methods of identifying agents that modulate the level of an endocannabinoid in a subject by assessing the capacity of a test substance to modulate the binding of intracellular fatty acid binding proteins with intracellular fatty acid binding proteins. The invention further provides methods of identifying agents for modulating the levels of endocannabinoids in a subject by testing the agents for their ability to modulate the expression of intracellular fatty acid binding proteins. The invention even further provides methods of identifying agents for treatment of neurological disorders by testing the agents for their ability to modulate the interaction of endocannabinoids with an intracellular fatty acid binding proteins.

BACKGROUND OF THE INVENTION

The following description summarizes information relevant to the present invention. It is not an admission that any of the information provided herein is prior art to the presently claimed invention, nor that any of the publications specifically or implicitly referenced are prior art to that invention.

Publications and other materials including patents and patent applications used to explain the specification are hereby incorporated by reference.

Cannabinoids include a group of terpenophenolic compounds present in *Cannabis* (*Cannabis sativa*). More broadly, the term relates to a group of substances that are structurally related to tetrahydrocannabinol (THC) or that bind to cannabinoid receptors.

Endocannabinoids are substances produced from within the body which also activate cannabinoid receptors. The first endocannabinoid that was identified was arachidonoyl ethanolamide (AEA). Another endocannabinoid that has been identified is 2-arachidonoyl glycerol (2-AG). Like $\Delta^9$-tetrahydrocannabinol, many of the actions of AEA and 2-AG are mediated through the cannabinoid receptors CB1 and CB2.

Cannabinoids have broad effects on the central nervous system (CNS) and influence, for example, movement, memory, nociception, endocrine regulation, thermoregulation, sensory perception, cognitive functions, and mood. Similarly, genetic and pharmacological studies have revealed a broad role for endocannabinoid signaling in a variety of physiological processes, including neuromodulator release, motor learning, synaptic plasticity, appetite, and pain sensation.

Overall, the effects of cannabinoids and endocannabinoids correlate with the distribution of CB1, one of the most abundant G-protein-coupled receptors in the central nervous system. Knockout CB1 and CB2 mice confirm the important role of the cannabinoid system (and by inference the endocannabinoids) in the above physiological responses as well as in mediating opiate addictive behavior, learning, and immunological responses.

In the CNS, the endocannabinoids AEA and 2-AG are believed to be synthesized on demand by postsynaptic neurons and to serve as retrograde neurotransmitters to presynaptically localized CB1. As with any other neurotransmitter, there are specific mechanisms for the inactivation of endocannabinoids. The inactivation of AEA occurs within cells and is primarily facilitated by the enzyme 'anandamide amidase', now known as FAAH, which hydrolysis AEA into arachidonic acid and ethanolamine. By metabolizing anandamide, FAAH maintains an inward concentration gradient that drives AEA's cellular accumulation. FAAH is expressed throughout the mammalian central and peripheral nervous systems and in many organs, including brain, spinal cord, liver, testis, kidney, retina, uterus, and placenta. It is usually found post synaptically in cell bodies.

SUMMARY OF THE INVENTION

In general, in a first aspect, the present invention features a method of modulating the level of an endocannabinoid in a cell or cell culture by culturing the cell in the presence of a compound that modulates the amount of the endocannabinoid that can be bound to a fatty acid binding protein expressed by the cell. Accordingly, the invention also provides a method for identifying an agent for treatment of a neurological disorder associated with an endocannabinoid. Embodiments of the invention may include one or more of the following features. In one embodiment, the agent increases the level of the endocannabinoid. In another embodiment, the agent reduces the level of the endocannabinoid. In an embodiment, the agent modulates binding of the endocannabinoid to the intracellular fatty acid binding protein. In another embodiment, the agent modulates expression of the intracellular fatty acid binding protein. In an embodiment of the invention, the endocannabinoid is anandamide (AEA) or 2-arachidonoylglycerol (2-AG). In another embodiment, the intracellular fatty acid binding protein is FABP3, FABP5, or FABP7. In yet another embodiment, the intracellular fatty acid binding protein is FABP5 and the endocannabinoid is AEA. In yet another embodiment, the intracellular fatty acid binding protein is FABP7 and the endocannabinoid is anandamide (AEA). In yet another embodiment, the intracellular fatty acid binding protein is FABP3 and the endocannabinoid is 2-arachidonoylglycerol (2-AG). In an embodiment of the invention, the agent is a small molecule. In yet another embodiment, the agent is a nucleic acid. In another embodiment, the nucleic acid is an antisense nucleic acid, a miRNA, or an siRNA. In yet another embodiment, the level of the endocannabinoid is modulated in the CNS.

The invention also provides a method of modulating the level of an endocannabinoid in a subject in need thereof by administering an effective amount of an agent that modulates the interaction of the endocannabinoid with an intracellular fatty acid binding protein. In one embodiment, the method involves administration of an agent that inhibits the interaction of the endocannabinoid with an intracellular fatty acid binding protein. In another embodiment, the method involves administration of a compound that reduces the amount of the endocannabinoid that can be bound or transported by the fatty acid binding protein by reducing the level of the fatty acid binding protein that is expressed by a cell. In one embodiment, the agent modulates the level of an endocannabinoid associated with a neurological disorder.

In another aspect, the present invention provides a method of identifying an agent that modulates endocannabinoid function by contacting a test agent with a fatty acid binding protein (FABP) expressed in the CNS, and detecting ligand binding to the FABP, wherein the agent is identified by its ability to modulate ligand binding to the FABP relative to binding of the ligand to the FABP in the absence of the agent. In an embodiment of the invention, the ligand is an endocannabinoid.

The invention also provides a method of identifying an agent useful for treatment of a neurological disorder by contacting a test agent with a fatty acid binding protein (FABP) expressed in the CNS, and detecting ligand binding to the FABP. The invention also provides a method of identifying an agent for treatment of a neurological disorder associated with an endocannabinoid by contacting a test agent with a fatty acid binding protein (FABP) expressed in the CNS, and detecting ligand binding to the FABP. In an embodiment of the invention, the neurological disorder affects at least one of movement, memory, mood, appetite, nociception, endocrine regulation, thermoregulation, sensory perception, and cognitive functions. In yet another embodiment, the neurological disorder is drug addiction, depression, compulsive behavior, neuropathic pain, or a movement disorder.

Embodiments of the invention may include one or more of the following features. In one embodiment, the fatty acid binding protein is FABP3, FABP5, or FABP7. In another embodiment, the agent inhibits binding of the endocannabinoid to the FABP. In yet another embodiment, the affinity of the agent for the FABP is greater than the affinity of the agent for an FABP that is expressed elsewhere in a host but substantially not expressed in the CNS. In yet another embodiment, the affinity of the agent for the FABP is greater than the affinity of the agent for one or more FABPs selected from FABP1, FABP2, FABP4, FABP6, FABP8, and FABP9. In another embodiment, the agent is selectively inhibits binding of an endocannabinoid to FABP3, FABP5, or FABP7.

In another aspect, the present invention provides a method of identifying an agent for modulating the level of an endocannabinoid in a subject by testing the agent for its ability to modulate expression of an intracellular fatty acid binding protein.

The invention provides a kit useful for identifying a substance that inhibits binding of a ligand to an FABP expressed in the CNS. In an embodiment of the invention, the kit comprises a ligand of the FABP useful as a control or in a competitive inhibition assay. In an embodiment of the invention, the ligand is an endocannabinoid, including, but not limited to, AEA or 2-AG. In an embodiment of the invention, the ligand is the compound BMS309403 or the compound BMS480404. In an embodiment of the invention, the FABP and/or the ligand is conjugated to a reporter moiety, including, but not limited to, a radiolabel, a fluorescence label, and enzyme, or an immunologically detectable label. Typically, the kit will contain or be packaged with instructions for use as described herein.

DETAILED DESCRIPTION OF THE INVENTION

Figure 1:
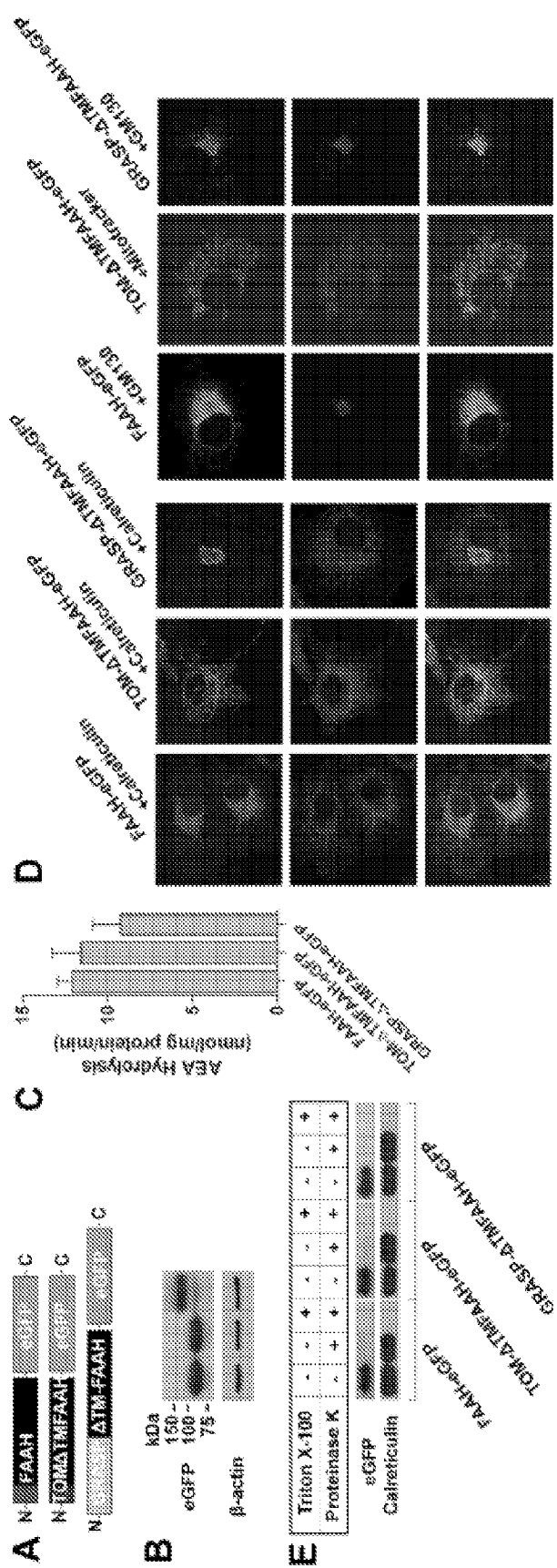
FIG. 1. Generation of FAAH variants with distinct subcellular localizations. (a) Constructs used in this study. FAAH-eGFP is shown with its N-terminal transmembrane helix (residues 1-29) in red, residues 30-579 in black, and eGFP in green. In TOM-ΔTMFAAH-eGFP, the N-terminal helix was replaced with the N-terminus of mouse TOM20 (blue, residues 1-33). In GRASP-ΔTMFAAH-eGFP, the Golgi resident protein grasp65 (grey) was fused to the N-terminus of ΔTM-FAAH-eGFP. (b) Western blot indicates similar protein levels in homogenates of COS-7 cells stably expressing FAAH-eGFP, TOM-ΔTMFAAH-eGFP or GRASP-ΔTMFAAH-eGFP. The blots were probed with eGFP antibodies with β-actin serving as a loading control. (c) Similar rates of [$^{14}$C] AEA hydrolysis (100 µM) were observed in COS7-FAAH-eGFP, TOM-ΔTMFAAH-eGFP and GRASP-ΔTMFAAH-eGFP homogenates (n=3). (d) FAAH fusion protein localization is restricted to specific organelles. Top panel shows FAAH-eGFP fusion proteins (green), middle panel depicts the marker of interest (red), and the bottom panel is the merged image (yellow). FAAH-eGFP localized to the ER and mostly overlapped with the ER marker, calreticulin. TOM-ΔTMFAAH-eGFP co-localized with the mitochondrial dye Mitotracker CM-H2Xros and was excluded from the ER. As confirmed by double labeling with GM130, GRASP-ΔTMFAAH-eGFP localized to the Golgi apparatus in COS-7 cells. Note that overexpression of GRASP-ΔTMFAAH-eGFP resulted in an enlargement of the Golgi apparatus. (e) Proteinase K protection analysis of FAAH-eGFP, TOM-ΔTMFAAH-eGFP and GRASP-ΔTMFAAH-eGFP proteins in membrane fractions of COS-7 cells. Membranes were either left untreated or were incubated with 500 µg/ml proteinase K in the presence or absence of 1% Triton X-100. Samples were subsequently resolved by SDS-PAGE and probed with eGFP and calreticulin antibodies.

Cannabinoids are a group of terpenophenolic compounds present in *Cannabis* (*Cannabis sativa*). More broadly, the term 'cannabinoids' refers to a group of substances that are structurally related to tetrahydrocannabinol (THC) or, alternatively, that bind to cannabinoid receptors. Endocannabinoids, on the other hand, are substances produced from within the body which also activate cannabinoid receptors. The first endocannabinoid that was identified was arachidonoyl ethanolamide (anandamide, AEA). Another endocannabinoid that has been identified is 2-arachidonoyl glycerol (2-AG). Like THC, many of the actions of AEA and 2-AG are mediated through the cannabinoid receptors CB1 and CB2.

In the CNS, AEA and 2-AG are believed to be synthesized and released on demand by postsynaptic neurons and to serve as retrograde neurotransmitters for cannabinoid CB1 receptors localized on presynaptic neurons. The endocannabinoid 2-AG is metabolized primarily by monoacylglycerol lipase (MAGL), an enzyme usually found in the presynaptic cell. AEA, on the other hand, is primarily inactivated and hydrolyzed into arachidonic acid and ethanolamine intracellularly by the enzyme 'fatty acid amide hydrolase,' also known as FAAH.

FAAH is expressed throughout the mammalian central and peripheral nervous systems and in many organs, including brain, spinal cord, liver, testis, kidney, retina, uterus, and placenta. It is usually found postsynaptically in cell bodies. It displays a monotopic membrane orientation, interacting with one leaflet of the lipid bilayer and is oriented towards the cytosolic side of the endoplasmic reticulum. FAAH knockout mice possess highly elevated (>15 fold to 30-fold) levels of AEA, palmitoylethanolamide (PEA) and related fatty acid amides, suggesting that FAAH is the principal enzyme mediating their catabolism in vivo.

AEA also belongs to the broader class of fatty acid amides (FAAs). Members of this class include, for example, AEA, N-oleoylethanolamine and N-palmitoylethanolamine, oleamide, and N-acyltaurines. Oleamide, an FAA, is structurally related to the endogenous cannabinoid anandamide. Oleamide accumulates in the cerebrospinal fluid during sleep deprivation and induces sleep in animals. It is likely that oleamide interacts with multiple neurotransmitter systems. N-acyltaurines, also belonging to the class of FAAs, have been isolated from the central nervous system and peripheral tissues. Like other biologically active amides in animals, the levels of these metabolites are controlled by the activity of FAAH. N-Arachidonylserine has also been detected in the brain. It has potent vasodilatory effects, amongst other biological effects. At least three other arachidonyl amino acids, of γ-aminobutyric acid, alanine and asparagine, occur naturally and also inhibit pain, suggesting that such biomolecules may be integral to pain regulation.

The peroxisome proliferator-activated receptors (PPARs) constitute a family of nuclear receptor proteins that function as transcription factors regulating the expression of genes. PPARs play essential roles in the regulation of cellular differentiation, development, and metabolism (carbohydrate, lipid, and protein). Ligands for PPARs include fatty acids.

Cannabinoids have broad effects on the central nervous system (CNS) and influence, for example, movement, memory, nociception, endocrine regulation, thermoregulation, sensory perception, cognitive functions, and mood. Similarly, genetic and pharmacological studies have revealed a broad role for endocannabinoid signaling in a variety of physiological processes, including neuromodulator release, motor learning, synaptic plasticity, appetite, and pain sensation. Overall, the effects of cannabinoids and endocannabinoids correlate with the distribution of CB1, one of the most abundant G-protein-coupled receptors in the central nervous system. Knockout CB1 and CB2 mice confirm the important role of the cannabinoid system (and by inference the endocannabinoids) in the above physiological responses as well as in mediating opiate addictive behavior, learning, and immunological responses.

Because of the central role endocannabinoids play in many crucial physiological and biological processes, there is a need for methods of modulating the level of endocannabinoids in a subject in need thereof, and, additionally, for example, for methods of identifying agents that modulate the level of endocannabinoids.

It has been discovered that fatty acid binding proteins (FABPs) function as intracellular carriers that shuttle cannabinoids (and by extension fatty acid amides (FAAs)) to FAAH where cannabinoids are hydrolyzed and degraded. Further, uptake of endocannabinoids (and by extension FAAs) by the cell and the subsequent hydrolysis of endocannabinoids (and by extension FAAs) are enhanced by FABPs, and inhibiting the interaction of endocannabinoids (and by extension FAAs) with FABPs reduces endocannabinoid (and by extension FAA) uptake and hydrolysis.

There are at least nine members of the FABP family, which share common sequence motifs, but have different patterns of tissue expression and differences in ligand selectivity and affinity for long chain fatty acids. An FABP that is expressed in the CNS means an FABP that is substantially expressed in brain or spinal cord, including B-FABP (FABP7), E-FABP (FABP5), and H-FABP (FABP-3). This is not meant to exclude an FABP that is also expressed outside of the CNS.

Fatty acid amides constitute a subgroup of fatty acids. Endocannabinoids constitute a subgroup of fatty acid amides. AEA and 2-AG are endocannabinoids.

Method of Modulating the Level of an Endocannabinoid

Thus, according to the present invention, there is provided a method of modulating endocannabinoid function in a subject in need thereof comprising administering an effective amount of an agent that modulates the interaction of the endocannabinoid with a fatty acid binding protein. In a preferred embodiment, the agent inhibits the interaction of the endocannabinoid with a fatty acid binding protein. Non-exclusive measures of endocannabinoid function include the amount of an endocannabinoid bound to a fatty acid binding protein, the amount of an endocannabinoid available to bind to an endocannabinoid receptor, and endocannabinoid mediated signaling through an endocannabinoid receptor. In an organism, additional non-exclusive measures include the level of an endocannabinoid in the central nervous system, (e.g., in cerebrospinal fluid) and measures of neurological function, such as mood, nociception, movement, sensory perception, and others as described herein.

The phrase "subject in need thereof" as used herein refers to any organism in need of treatment, or requiring preventative therapy to prevent a condition resulting from lower or higher than normal levels of endocannabinoids in the organism, with the methods of the invention. The subject may be a plant or an animal. The subject animal includes fish, birds, or mammals. The subject may be livestock, such as cattle, swine, sheep, poultry, and horses, or pets, such as dogs and cats. In an embodiment of invention, the subject is a human.

The term "effective amount" refers to the amount of an agent that is effective in modulating the level of an endocannabinoid in a subject. In a preferred embodiment, the agent increases the level of an endocannabinoid by reducing endocannabinoid degradation. In one such embodiment, an effective amount of an agent reduces endocannabinoid degradation by at least 20% or at least 50% or at least 80%. In another embodiment, an effective amount of an agent increases the level of an endogenous cannabinoid by at least about 25%, or at least 50%, or at least 70%. In another embodiment, an effective amount of an agent raises the level of an endogenous cannabinoid to at least two-fold, or at least 5-fold, or at least 10-fold of the untreated level. In another embodiment, the agent reduces the level of an endocannabinoid by increasing endocannabinoid degradation, for example, by increasing the level of a fatty acid binding protein and/or activating binding of an endocannabinoid to an fatty acid binding protein. In one such embodiment, an effective amount of an agent increases endocannabinoid degradation by at least 20% or at least 50% or at least 80%. In another embodiment, an effective amount of an agent reduces the level of an endogenous cannabinoid by at least about 25%, or at least 50%, or at least 70%. In another embodiment, an effective amount of an agent reduces the level of an endogenous cannabinoid to at least two-fold, or at least 5-fold, or at least 10-fold of the untreated level.

The term "endocannabinoid" includes any molecule that is produced from within the a subject and that activates cannabinoid receptors. Examples of such receptors are CB1 and CB2. In one embodiment of the invention, for example, the endocannabinoid is arachidonoyl ethanolamide (AEA). In another embodiment of the invention, for example, the endocannabinoid is 2-arachidonoyl glycerol (2-AG).

The term "agent" is employed herein to refer to any kind of compound or combination of compounds. In one embodiment of the invention the agent is a small molecule. In another embodiment of the invention, the agent is a biological molecule, including, but not limited to, a protein or a peptide or a nucleic acid. In one embodiment, the nucleic acid is an interfering RNA. The term "interfering RNA" is employed herein to refer to small interfering RNAs (siRNAs), short hairpin RNAs (shRNAs), microRNAs (miRNAs), antisense oligonucleotides, ribozymes, or any RNA-based molecule that interferes with the expression of a protein from its corresponding gene. In another embodiment, the agent increases cannabinoid binding in a cell by activating cannabinoid binding by an FABP and or increasing the amount of the FABP. In another embodiment of the invention, the agent of the present invention is oleic acid. In another embodiment, the agent is docosahexaenoic acid. In another embodiment, the agent is the compound BMS309403 or a related compound. BMS309403 and related compounds are disclosed in WO 00/59506. BMS309403 is a competitive inhibitor of FABPs with reported $IC_{50}$ values of 250 nm and 350 nm for FABP3 and FABP5, respectively (Furuhashi, M. et al., 2008, Nat. Rev. Drug. Discov. 7:489-503; Sulsky, R. et al., 2007, Bioorg. Med. Chem. Lett. 17:3511-5). In another embodiment, the agent is the compound BMS480404 or a related compound. BMS480404 and related compounds are disclosed in WO 00/043624 and are dual inhibitors of FABP-4 (aP2) and k-FABP. (See, also, McConnell, P. A. et al., 2006, J. Med. Chem. 49:5013-7).

According to the invention, inhibitory polynucleotides may be used to inhibit expression of one or more FABPs Inhibitory polynucleotides are polynucleotides or polynucleotide analogs that are complimentary to a portion of a target gene and reduce or prevent expression of the target gene product (e.g., mRNA or protein). Inhibitory polynucleotides are typically greater than 10 bases or base pairs in length and are composed of ribonucleotides or deoxynucleotides or a modified form of either type of nucleotide, and may be single and/or double stranded. Inhibitory polynucleotides may by modified to increase stability and/or enhance delivery of the inhibitory polynucleotide to the cytosol of target cells. Inhibitory polynucleotides include chemically modified polynucleotides. Chemical modification includes changes to the inhibitory polynucleotide backbone, replacement of one or more nucleotides with nucleotide analogues, and addition of conjugates to the polynucleotide. Thus, modifications include 2'O-methyl RNA, phosphorothioate bonds, locked nucleic acids as well as addition of moieties such as cholesterol, peptides, polyethylene glycol, and fatty acids.

Polynucleotide analogs include, but are not limited to peptide nucleic acids (PNAs) and morpholinos. PNAs comprise naturally-occurring DNA or RNA bases (i.e., adenine, thymine, cytosine, guanine, uracil) or artificial bases (i.e., bromothymine, azaadenines, azaguanines) attached to a peptide backbone through a suitable linker (e.g., amide, thioamide, sulfinamide or sulfonamide linkages). PNAs bind complementary DNA or RNA strands and can be utilized in a manner similar to antisense oligonucleotides to block the translation of specific target mRNA transcripts. PNA oligomers can be prepared according to the method provided by U.S. Pat. No. 6,713,602. U.S. Pat. No. 6,723,560 describes methods for modulating transcription and translation using sense and antisense PNA oligomers, respectively. PNAs may be obtained from commercial sources such as Panagene, Inc. PNAs are typically about 10 to about 30 subunits in length. The PNAs may also be about 15 to about 25 subunits in length. The PNAs may also be about 14 to about 20 subunits in length. The PNAs may also be about 16 to about 18 subunits in length.

Morpholino oligomers are short chains of about 10 to about 30 morpholino subunits. Morpholinos may also be about 15 to about 25, or about 18 to about 22 subunits long. Each subunit is comprised of a nucleic acid base, a morpholine ring and a non-ionic phosphorodiamidate intersubunit linkage. Morpholinos do not degrade their RNA targets, but instead act via a steric blocking mechanism. Systemic delivery into cells in adult organisms can be accomplished by using covalent conjugates of Morpholino oligos with cell penetrating peptides. An octa-guanidinium dendrimer attached to the end of a Morpholino can deliver the modified oligonucleotide (called a Vivo-Morpholino) from the blood to the cytosol. (Moulton, J. D., Jiang S. (2009). Gene Knockdowns in Adult Animals: PPMOs and Vivo-Morpholinos. *Molecules,* 14 (3): 1304-23; Morcos, P. A., Li Y. F., Jiang S. (2008). Vivo-Morpholinos: A non-peptide transporter delivers Morpholinos into a wide array of mouse tissues. *BioTechniques* 45 (6):616-26).

An inhibitory polynucleotide is complimentary or partially complimentary to the target gene mRNA and the complimentary or partially complimentary region of the target gene mRNA may be in the in the 5' untranslated region (UTR), 3' UTR, and/or in the coding region. An inhibitory polynucleotide may induce RNA interference (RNAi), which is a mechanism of gene-specific silencing that employs sequence-specific small interfering RNA (siRNA) to target and degrade the target gene-specific mRNA prior to translation. siRNAs are double-stranded RNA molecules, typically about 19 to about 23 nucleotides in length and having a 2 nucleotide overhang at the 3' end of each strand. Methods for designing specific siRNAs based on an mRNA sequence are well known in the art (see e.g., Brummelkamp, T. R. et al. (2002) A system for stable expression of short interfering RNAs in mammalian cells. *Science* 19, 550-553; Ui-Tei, K. et al. (2004) Guidelines for the selection of highly effective siRNA sequences for mammalian and chick RNA interference. *Nucleic Acids Res.* 32, 936-948; Hohjoh H. (2004) Enhancement of RNAi activity by improved siRNA duplexes. *FEBS Lett.* 557, 193-8; and Yuan, B., et al. siRNA Selection Server: an automated siRNA oligonucleotide prediction server. (2004) *Nucleic Acids Res.* 32, W130-134). In addition, design algorithms are available on the websites of many commercial vendors that synthesize siRNAs, including Ambion, Clontech, Dharmacon, GenScript, and Qiagen.

Small interfering RNAs can be expressed in the form of short, hairpin loop polynucleotides known as short hairpin RNAs (shRNAs) comprising the siRNA sequence of interest and a hairpin loop segment. Short hairpin RNAs are available through commercial vendors, which often provide online algorithms useful for designing shRNAs (e.g., Clontech, Invitrogen, ExpressOn, Gene Link, and BD Biosciences). When expressed in a cell, shRNA is rapidly processed by intracellular machinery into siRNA. Expression of shRNAs may be accomplished by ligating the DNA sequence corresponding to the shRNA into an expression construct, for example the cloning site of a double-stranded RNA (dsRNA) expression vector. Expression may be driven by RNA polymerase III promoters. Expression vectors may be plasmid vectors including retrovirus, lentivirus, adenovirus, and adeno-associated virus based systems. Vectors for expression of shRNAs are commercially available from vendors such as Clontech, Invitrogen, Millipore, Gene Therapy Systems, Ambion and Stratagene. Methods for DNA and RNA manipulations, including ligation and purification, are well known to those skilled in the art (See e.g., Sambrook, J. and Russel, D. W., (2001) Molecular Cloning: A Laboratory Manual, Third Edition. Cold Spring Harbor Laboratory Press, Cold Spring Harbor, N.Y.; and Current Protocols in Molecular Biology, (2001) John Wiley & Sons, Inc.).

Delivery of inhibitory polynucleotides may be local (i.e., to the site of the cell mass or affected tissue) or systemic (i.e., delivery to the circulatory or lymphatic systems). Local injection avoids many of the difficulties associated with intravenous administration, such as rapid elimination. In addition, helper molecules (for example, cationic lipids or polymers) or physical methods (for example electroporation, sonoporation, or hydrodynamic pressure) can be employed to facilitate intracellular entrance of the inhibitory polynucleotide. In addition, local production of inhibitory polynucleotides such as siRNA by genes encoding for shRNA can ensure prolonged levels of the dsRNA in the target cells.

In addition, the inhibitory polynucleotide may be complexed with cationic lipids, cholesterol, peptides, polyethyleneimine, and/or condensing polymers or packaged in a liposome, nanoparticle, virus, bacteria, or in a donor cell expressing one or more connexin proteins. In one embodiment the donor cell is an immune privileged cell such as a MSC. (see, e.g., Xie, F. Y., et al. (2006). Harnessing in vivo siRNA delivery for drug discovery and therapeutic development. *Drug Discovery Today*, 11:67-73; Oliveira, S. et al. (2006) Targeted Delivery of siRNA. *J. Biomed. Biotech.* 2006:1-9; Whitehead, K. A., et al. (2009) Knocking Down Barriers; Advances in siRNA Delivery. *Nature Reviews*, 8:129-138). The inhibitory polynucleotide may be targeted to the cell mass by associating the inhibitory polynucleotide to a targeting molecule. The targeting molecule may be linked to the inhibitory polynucleotide by a covalent bond or may be associated ionically or by integration into the targeting mechanism (e.g., as part of the liposome, nanoparticle, or expressed on the surface of a donor cell). Targeting molecules include antibodies, and cell-penetrating peptides.

Nonlimiting examples of interfering RNAs useful for inhibiting expression of FABPs include, but are not limited to, accuggaagcuaguggacagcaagaauuu (SEQ ID NO:1), agcaugaccaagccuaccacaaucaucga (SEQ ID NO:2), agcaccuucaagaacacagagaucagcuu (SEQ ID NO:3), and gcagaugacaggaaggucaaguccauugu (SEQ ID NO:4) for FAB3; gccacaguucagcagcuggaaggaagaug (SEQ ID NO:5), cugguggacagcaaaggcuuugaugaaua (SEQ ID NO:6), aguuugaagaaaccacagcugauggcaga (SEQ ID NO:7), and gaacaaugucaccuguacucggaucuaug (SEQ ID NO:8) for FABP5, and ugguggaggcuuucugugcuaccuggaag (SEQ ID NO:9), aggacucucagcacauucaagaacacgga (SEQ ID NO:10), aacuguaagucuguuguuagccuggaugg (SEQ ID NO:11), and ugguugcuguucgccacuaugagaaggca (SEQ ID NO:12) for FABP7. A single interfering RNA may be selected for a single gene locus, or a set of interfering RNAs for that locus can be used. Such interfering RNAs are readily commercially available in the form or siRNAs, shRNAs, and in vectors for transient and stable transfection. Naked or modified siRNAs can be stable for extended periods, for example up to two weeks in cerebrospinal fluid (CSF).

In the context of this invention, the term small molecule refers to small organic compounds, such as heterocycles, peptides, saccharides, steroids, and the like. The small molecule modulators preferably have a molecular weight of less than about 1500 Daltons, and more preferably less than about 500 Daltons. The compounds may be modified to enhance efficacy, stability, pharmaceutical compatibility, and the like. Candidate modulator compounds from libraries of synthetic or natural compounds can be screened. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). Combinatorial libraries are available or can be prepared according to known synthetic techniques. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds may be further modified through conventional chemical and biochemical techniques.

The phrase "modulating the level" is employed herein to refer to increasing the level or decreasing the level. The level of a molecule, for example the level of an endocannabinoid in a subject, may be the concentration of the molecule in a sample volume. Accordingly, "increasing the level" or "decreasing the level" may mean increasing the concentration or decreasing the concentration.

The phrase "inhibits the interaction" is employed herein to refer to any disruption, partial or total, of the natural effect of FABPs on the metabolism of endocannabinoids.

Endocannabinoids, in a subject or elsewhere, may be detected and their amount and concentration measured by any method commonly known in the art. This includes, for example, methods involving mass spectrometry, high pressure liquid chromatography (HPLC), combined gas chromatography-mass spectrometry, and liquid chromatography-atmospheric pressure chemical ionization-mass spectrometry (see for example De Marchi et al., *Lipids Health Dis.* 2:5, 2003). The modulation of the level of a compound, for example the increase or decrease of the concentration of an endocannabinoid in a subject, may be measured by detecting the compound in samples taken at different times. Endocannabinoids can be measured in samples taken from, for example, cerebrospinal fluid or blood.

In one embodiment of the present invention, the agent used for modulating the level of an endocannabinoid in a subject modulates binding of the endocannabinoid to the fatty acid binding protein. The binding of endocannabinoids to proteins like fatty acid binding proteins, for example, may be detected and quantified according to methods commonly known in the art (see for example Glatz et al., *J. Biol. Chem.*, 259:4295-4300, 1984; and Morrow & Martin, *J. Lipid Res.*, 24:324-331, 1983). Accordingly, examples of such methods may include or involve incubation of FABPs with radio-labeled endocannabinoids in the presence or absence of compounds to be tested with respect to their effect on the binding or interaction between the FABPs and endocannabinoids. Examples of such methods may further include the subsequent separation of FABP-bound and unbound endocannabinoids and quantification of endocannabinoids bound to FABPs in the presence or in the absence of test-compounds.

In another embodiment, the agent used for modulating the level of an endocannabinoid in a subject modulates the interaction of an FABP that facilitates transport of the endocannabinoid with an enzyme that degrades the endocannabinoid. Such enzymes may be membrane bound or cytoplasmic, including, but not limited to, fatty acid amide hydrolase (FAAH), and cytoplasmic monoacylglycerol lipase (MAGL). Further, any of these approaches my used in vivo, ex vivo, or in vitro.

In one embodiment of the present invention, the agent used for modulating the level of an endocannabinoid in a subject modulates expression of the fatty acid binding protein. The expression of genes like those encoding fatty acid binding proteins, for example, may be detected and quantified according to methods commonly known in the art (see for example Sambrook et al., Molecular Cloning: A Laboratory Manual (Third Edition), Cold Spring Harbor Press, 2001). Examples of such methods include, or involve, quantitative reverse transcription-polymerase chain reaction (RT-PCR), real-time PCR, Northern blotting, Western blotting, immunohistochemistry, fluorescence activated cell sorting (FACS). For example, expression of a FABP can be ascertained by detecting the FABP protein, the level of mRNA encoding the protein, or expression of a hybrid reporter gene comprising regulatory elements of the FABP and encoding a product that facilitates detection, including but not limited to a fluorescent protein. Further, any of these approaches my used in connection with an in vivo, ex vivo, or in vitro experimental setup.

The term "fatty acid binding protein" includes, for example, fatty acid binding protein 1 (FABP 1), fatty acid binding protein 2 (FABP 2), fatty acid binding protein 3 (FABP 3), fatty acid binding protein 4 (FABP 4), fatty acid binding protein 5 (FABP 5), fatty acid binding protein 6 (FABP 6), fatty acid binding protein 7 (FABP 7), fatty acid binding protein 8 (FABP 8), fatty acid binding protein 9 (FABP 9), fatty acid binding protein 10 (FABP 10), fatty acid binding protein 11 (FABP 11), fatty acid binding protein 5-like 1 (FABP 5-like 1), fatty acid binding protein 5-like 2 (FABP 5-like 2), fatty acid binding protein 5-like 3 (FABP 5-like 3), fatty acid binding protein 5-like 4 (FABP 5-like 4), fatty acid binding protein 5-like 5 (FABP 5-like 5), fatty acid binding protein 5-like 6 (FABP 5-like 6), and fatty acid binding protein 5-like 7 (FABP 5-like 7) (see Chmurzynska et al., J Appl Genet, 47:39-48, 2006).

In one embodiment of the present invention, the fatty acid binding protein is FABP 3. In another embodiment of the present invention, the fatty acid binding protein is FABP 5. In still another embodiment of the present invention, the fatty acid binding protein is FABP 7.

In one embodiment of the present invention, the fatty acid binding protein is FABP 5 and the endocannabinoid is AEA. In another embodiment of the present invention, the fatty acid binding protein is FABP 7 and the endocannabinoid is AEA. In still another embodiment of the present invention, the fatty acid binding protein is FABP 3 and the endocannabinoid is 2-AG.

In an embodiment of the present invention, the fatty acid binding protein is FABP 5, the endocannabinoid is AEA, and the agent is the compound BMS309403 or the compound BMS-480404.

The dosage of an agent that is administered to a subject in need thereof may vary, depending on the reason for use and the individual subject. The dosage may be adjusted based on the subject's weight, the age and health of the subject, and tolerance for the compound or composition.

In the context of the present invention, the acronym CNS means "central nervous system."

In the context of the present invention, the term "neurological disorder" includes any medical condition that involves the nervous system.

The amount of therapeutic agent to be used depends on many factors, including, but not limited to, the identity of the FABP target, the FABP ligand (e.g., the fatty acid that binds to the FABP, the specificity of the therapeutic agent for the FABP, and the extent to which it is desired to inhibit the binding of the FABP to the FABP ligand. For example, the 40 mg/kg of bodyweight/day of compound BMS309403 has been used to inhibit FABP4 function in mice (Furuhashi et al., Nature, 447(7147):959-65, 2007).

Other dosages may include about 2 mg/kg of bodyweight/day, about 5 mg/kg of bodyweight/day, about 10 mg/kg of bodyweight/day, about 15 mg/kg of bodyweight/day, about 20 mg/kg of bodyweight/day, about 25 mg/kg of bodyweight/day, about 30 mg/kg of bodyweight/day, about 40 mg/kg of bodyweight/day, about 50 mg/kg of bodyweight/day, about 60 mg/kg of bodyweight/day, about 70 mg/kg of bodyweight/day, about 80 mg/kg of bodyweight/day, about 90 mg/kg of bodyweight/day, about 100 mg/kg of bodyweight/day, about 125 mg/kg of bodyweight/day, about 150 mg/kg of bodyweight/day, about 175 mg/kg of bodyweight/day, about 200 mg/kg of bodyweight/day, about 250 mg/kg of bodyweight/day, about 300 mg/kg of bodyweight/day, about 350 mg/kg of bodyweight/day, about 400 mg/kg of bodyweight/day, about 500 mg/kg of bodyweight/day, about 600 mg/kg of bodyweight/day, about 700 mg/kg of bodyweight/day, about 800 mg/kg of bodyweight/day, and about 900 mg/kg of bodyweight/day. Routine experimentation will determine the appropriate value for each patient by monitoring the compound's effect on serum endocannabinoid levels, which can be frequently and easily monitored. The agent can be administered once or multiple times per day. The frequency of administration may vary from a single dose per day to multiple doses per day. Preferred routes of administration include oral, intravenous and intraperitoneal, but other forms of administration may be chosen as well.

The effective amount of an agent according to the present invention may be administered along any of the routes commonly known in the art. This includes, for example, (1) oral administration; (2) parenteral administration, for example, by subcutaneous, intramuscular or intravenous injection; (3) topical administration; or (4) intravaginal or intrarectal administration; (5) sublingual or buccal administration; (6) ocular administration; (7) transdermal administration; (8) nasal administration; and (9) administration directly to the central nervous system (CNS).

The effective amount of an agent according to the present invention may be formulated together with one or more pharmaceutically acceptable excipients. The active ingredient and excipient(s) may be formulated into compositions and dosage forms according to methods known in the art. These compositions and dosage forms may be specially formulated for administration in solid or liquid form, including those adapted for the following: (1) oral administration, for example, tablets, capsules, powders, granules, pastes for application to the tongue, aqueous or non-aqueous solutions or suspensions, drenches, or syrups; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of the subject with toxicity, irritation, allergic response, or other problems or complications, commensurate with a reasonable benefit/risk ratio.

The phrase "pharmaceutically-acceptable excipient" as used herein refers to a pharmaceutically-acceptable material, composition or vehicle, such as a liquid or solid filler, diluent, carrier, manufacturing aid (e.g., lubricant, talc magnesium, calcium or zinc stearate, or stearic acid), solvent or encapsulating material, involved in carrying or transporting the therapeutic compound for administration to the subject. Each excipient should be "acceptable" in the sense of being compatible with the other ingredients of the formulation and not injurious to the subject. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

Excipients are added to the composition for a variety of purposes. Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the subject's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions of the present invention, the modulator of a eukaryotic pathogen's adenylyl cyclase and any other solid excipients are dissolved or suspended in a liquid carrier such as water, water-for-injection, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste. Flavoring agents and flavor enhancers may make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate or sodium acetate. Selection of excipients and the amounts used may be readily determined by the formulation scientist based upon experience and consideration of standard procedures and reference works in the field.

Solid and liquid compositions may also be dyed using any pharmaceutically acceptable colorant to improve their appearance and/or facilitate patient identification of the product and unit dosage level.

The dosage form of the present invention may be a capsule containing the composition, for example, a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling may include any of the aforementioned blends and granulates that were described with reference to tableting; however, they are not subjected to a final tableting step.

In the context of the present invention, the effective amount of the agent modulating the level of an endocannabinoid may be administered alone or in combination with one or more of other therapeutic agents. In a combination therapy, the effective amount of the agent modulating the level of an endocannabinoid may be administered before, during, or after commencing therapy with another agent, as well as any combination thereof, i.e., before and during, before and after, during and after, or before, during and after commencing the additional therapy.

Method of Identifying an Agent for Modulating the Level of an Endocannabinoid

According to the present invention, there is provided a method of identifying an agent for modulating the level of an endocannabinoid in a subject comprising testing the agent for its ability to modulate binding of the endocannabinoid with an intracellular fatty acid binding protein. Preferably, the fatty acid binding protein is one or more of FABP3, 5, and 7. According to the invention, modulating binding to an intracellular fatty acid binding protein is accomplished by modulating the amount of a fatty acid binding protein available to interact with the endocannabinoid, or by modulating the binding interaction itself. The amount of a fatty acid binding protein, or the binding of an endocannabinoid with an intracellular fatty acid binding protein may be detected and quantified according to methods disclosed herein as well as method otherwise commonly known in the art. The mechanism by which the agent modulates the interaction is not limited. For example, the agent may bind to the endocannabinoid or the FABP. In an embodiment of the invention, the agent binds to an FABP with an affinity of at least about 1000 nM, or at least about 500 nM, or at least about 250 nM, or at least about 100 nM, or at least about 50 nM, or at least about 10 nM, or at least about 5 nM, or at least about 2 nM. In an embodiment of the invention, the agent has a higher affinity for FABP3, 5, or 7 than for other FABPs. In an embodiment of the invention, the agent selectively inhibits binding of the endocannabinoid to the FABP. For example, the agent inhibits binding of the endocannabinoid to the FABP with an $IC_{50}$ that is lower than the $IC_{50}$ of inhibition of binding of an endogenous fatty acid to an FABP that is expressed elsewhere, but not substantially expressed in the CNS. Such FABPs that are not substantially expressed in the CNS include FABP1, 2, 4, 6, 8 and 9.

In yet another embodiment, wherein the FABP is expressed in neural tissue and elsewhere, the agent inhibits endocannabinoid binding to the FABP (e.g., in neural tissue) and binding of another endogenous fatty acid to the FABP (i.e., in non-neural tissue). In one such embodiment, the $IC_{50}$ for inhibition of endocannabinoid binding to the FABP by the agent is lower than the $IC_{50}$ for inhibition of binding of an endogenous fatty acid present in non-neural tissue to the FABP. In another such embodiment, inhibition of binding of the endocannabinoid to the FABP reduces endocannabinoid function, while inhibition of binding of the endogenous fatty acid present in non-neural tissue to the FABP is also reduced, but not enough to substantially effect the function of the fatty acid present in non-neural tissue.

In one embodiment, the present invention provides for identifying a modulator of endocannabinoid function comprising contacting, in vitro, a FABP expressed in the CNS with a solution comprising a test agent under conditions suitable for binding of an FABP ligand to the FABP, and measuring the amount of one or more of the bound test agent or bound FABP (i.e., the test agent-FABP complex), the unbound FABP, and the unbound test agent. As discussed above, the FABP used in the method can be FABP3, FABP5, or FABP7, as well as fragments, mutants or derivatives of the foregoing, so long as they are capable of binding an endocannabinoid. To determine the binding affinity of test agent and the FABP, binding is measured multiple times using different concentrations of the test agent or the FABP. Binding of the test agent to the FABP can be compared with binding of a natural ligand of the FABP, such as AEA, 2-AG, docosahexaenoic acid, or oleic acid. The method can be performed entirely in the liquid phase, using for example reagents that exhibit fluorescence quenching when bound, or the binding interaction can be determined on a solid support.

In another embodiment of the invention, a method for identifying a modulator of endocannabinoid function is provided which comprises contacting, in vitro, a FABP expressed in the CNS with a solution comprising a test agent and a natural or artificial ligand of the FABP, under conditions suitable for binding of the FABP and the FABP ligand, and measuring the amount of one or more of the test agent-FABP complex, the FABP ligand-FABP complex, the unbound test agent, and the unbound ligand. A lower level of bound FABP ligand in the presence of the test reagent is correlated with an ability of the test agent to inhibit ligand-FABP interaction, and thus increase endocannabinoid function.

In one non-limiting example, a fatty acid binding protein (e.g., FABP5) or a fatty acid binding protein ligand (e.g., AEA) is detectably labeled. In one embodiment, the label is a fluorescent label and fluorescence quenching associated with ligand-receptor binding can be determined. In another embodiment, the ligand of the fatty acid binding protein is radiolabeled and binding (or inhibition) of the ligand to a fatty acid binding protein is determined.

The invention also provides a method for identifying a modulator of the interaction between an FABP expressed in the CNS and an enzyme that degrades an endocannabinoid that binds the FABP, thus identifying a modulator of endocannabinoid function. The method comprises contacting, in vitro, a FABP expressed in the CNS, an endocannabinoid, an enzyme that degrades the endocannabinoid, and a test agent. A reduction in the degradation of the endocannabinoid in the presence of the test agent is correlated with an ability of the test agent to increase endocannabinoid function. To confirm that the test agent modulates the interaction of the FABP and the degradative enzyme (e.g., FABP modulated diffusion of an endocannabinoid to the degradative enzyme) and is not an direct inhibitor of the degradative enzyme itself, it may be desired to also contact the endocannabinoid and the degradative enzyme with the test agent.

Of particular interest are FABPs expressed in the CNS, including FABP3, FABP5, and FABP7. According to the invention, FABPs or fatty acid amide-binding derivatives of the FABPs can be used to identify endocannabinoid modulators. FABP derivatives include FABP fragments, mutants, fusion proteins, and chemically modified derivatives. The FABPs may be modified with a detectable label, such as an enzymatic, fluorescent, isotopic, or affinity label to allow for immobilization or detection of the protein.

According to the invention, three-dimensional structural information from an FABP can be used in structure based drug design. Structure based drug design refers to the use of computer simulation to predict a conformation of a peptide, polypeptide, protein, or conformational interaction between a peptide or polypeptide, and a therapeutic compound. For example, generally, for a protein to effectively interact with a therapeutic compound, it is necessary that the three dimensional structure of the therapeutic compound assume a compatible conformation that allows the compound to bind to the protein in such a manner that a desired result is obtained upon binding. Further, knowledge of the three dimensional structure of a complex of an FABP with a ligand, and particularly the structural coordinates of atoms of a ligand and its binding site on the FABP enables a skilled artisan to design a therapeutic compound having such a compatible conformation.

Three dimensional structures of numerous FABPs, with and without bound ligand, are known in the art. See, e.g., Furuhashi et al., 2008, Nat Rev Drug Discov. 7:489-503. Structural coordinates of pertinent fatty acid binding proteins include the following PDB data sets:

| Fatty Acid Binding Protein | PDB code | |
|---|---|---|
| | unliganded | with ligand |
| FABP-3 (human) | 1g5w 2hmb | 1hmr; 1hms; 1hmt (C18 fatty acids) |
| FABP-5 (human) | 1b56 | |
| FABP-7 (human) | 1jjx | 1fe3 (oleic acid) 1fdq (docosahexaenoic acid (DHA)) |

The three-dimensional models are useful for screening, designing, and/or modifying inhibitor candidates in silico. Virtual libraries of compounds can be screened with the assistance of a computer. The compounds thus identified can be synthesized and further assayed for the ability to inhibit binding of a FABP with a ligand of the FABP. Another way to evaluate binding interactions of a putative inhibitor with an FABP is by NMR or X-ray crystallography.

Test compounds can be pharmacologic agents already known in the art or can be compounds previously unknown to have pharmacological activity. The compounds can be naturally occurring or designed in the laboratory. Test compounds can be obtained using combinatorial libraries, including but not limited to solid phase and solution libraries of small molecules and biological molecules.

In one aspect of the invention, the agent that is effective of inhibiting the interaction of an endocannabinoid with a fatty acid binding protein may be a small molecule. In this context, the term small molecule refers to small organic compounds, such as heterocycles, peptides, saccharides, steroids, and the like. The small molecule modulators preferably have a molecular weight of less than about 1500 Daltons, and more preferably less than about 500 Daltons. The compounds may be modified to enhance efficacy, stability, pharmaceutical compatibility, and the like. Candidate inhibitor compounds can be screened from libraries of synthetic or natural compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). Usually, atomic coordinates of the compounds in the libraries are also available, and can be used in virtual screens. Combinatorial libraries are available or can be prepared according to known synthetic techniques. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds may be further modified through conventional chemical and biochemical techniques.

Useful biological agents, such as polypeptides or antibodies or antibody fragments can also be identified by screening of libraries, as is known in the art. Such polypeptides are generally 30 amino acids or less, and can be, for example, from 4 to 20 amino acids, or from 5 to 15 amino acids, or from 7 to 10 amino acids. The structure of the polypeptides can be constrained, for example by disulfide bonds between included cysteine residues, and can be cyclic. Antibody fragments include, but are not limited to, Fv, single chain Fv (scFv), Fab, F(ab)$_2$', single domain antibodies, intrabodies, and other artificial antibody-like binding proteins.

Other types of libraries may also be employed, for example, any sort of synthetic polymers that can be screened and optionally, their structure or sequence determined. Numerous methods have been devised for generation of chemical diversity and mass screening of libraries. To simplify identification of library elements of interest, many libraries have the feature that synthesis steps are encoded. For example, in phage display, the displayed peptide is encoded in the genome encapsulated by the phage particle. Amino acid sequences of peptides identified by screening procedures are easily determined by sequencing a small predetermined part of the genome.

In another example, it has been demonstrated that peptides can be generated in numbers several orders of magnitude greater than by conventional one-at-a-time methods by synthesis on polyethylene rods or pins, arranged, for example, in a microtiter plate format. The pin technology is representative of techniques that generate libraries of single compounds in a spatially-differentiated manner. An alternative approach, to rapidly prepare large mixtures of compounds, is the split-pool approach (e.g., Houghten, R. A., 1985, Proc. Natl. Acad. Sci. U.S.A., 82:5131-5135) where a solid support material (e.g., beads) is physically segregated into equal portions for coupling to each of the individual initial reactants. This affords uniform coupling since competition between reactants is eliminated. The individual polymers are combined in a single vessel for washing and deprotection and then divided again into individual portions for the next coupling. Using this approach, a complete set of possible molecular combinations is rapidly prepared in approximately equimolar amounts. Coincident with coupling reactions, "identifier" tags can be attached to the solid support material. The structure of the molecule on any bead identified through screening is obtained by decoding the identifier tags. Numerous methods of tagging the beads have now been reported.

Inhibitors further include polymers of peptide-like molecules, and libraries of such molecules can be screened in the manner of antibodies and peptides. Non-limiting examples of peptide-like molecules include peptides composed partially or completely of D-amino acids, and peptoids. Peptoid libraries are a collection of N-substituted glycines as peptoid monomers which are assembled in a modular fashion. (Zuckermann, R. N. et al, 1994, J. Med. Chem., 37:2678-2685). The structures of the resulting compounds are unique, display unique binding properties, and incorporate the important functionalities of peptides in a novel backbone. Furthermore, studies suggest this class of compounds is resistant to enzymatic breakdown.

In one aspect of the invention, the agent that inhibits the interaction of an endocannabinoid with a FABP may be an aptamer, which are oligonucleic acid molecules that bind a specific target molecule. They can be synthesized specifically or selected from a pool using various screening methods known in the art for example a yeast two-hybrid system.

In binding and inhibition assays, either the test compound or the FABP can be labeled with a detectable label. The label can be fluorescent, chemiluminescent, or radioisotopic. Examples of enzymatic labels include horseradish peroxidase and alkaline phosphatase. Alternatively, binding of a test compound to a FABP can be detected or measured using technology that directly senses specific interaction without labels. One example is bimolecular interaction analysis (BIA), which is available commercially (e.g., BIAcore™).

The invention also provides a cellular assay for identifying a modulator of endocannabinoid function that binds to an FABP and modulates binding of the FABP to an endocannabinoid. The method can be used to identify an activator or inhibitor of endocannabinoid function. In one embodiment, an FABP, such as, for example, FABP-3, FABP-5, or FABP-7, is expressed at a higher level in a test cell relative to a control cell in which it is expressed at a lower level or not at all. The test cell and the control cell are contacted with an endocannabinoid and degradation of the endocannabinoid is monitored. Test substances that increase degradation of the endocannabinoid in the test cell to a greater extent that in the control cell are activators of the FABP, and activators of endocannabinoid function in a cell. Test substances that decrease degradation of the endocannabinoid in the test cell to a greater extent that in the control cell are inhibitors of the FABP, and inhibitors of endocannabinoid function in a cell.

Figure 3:
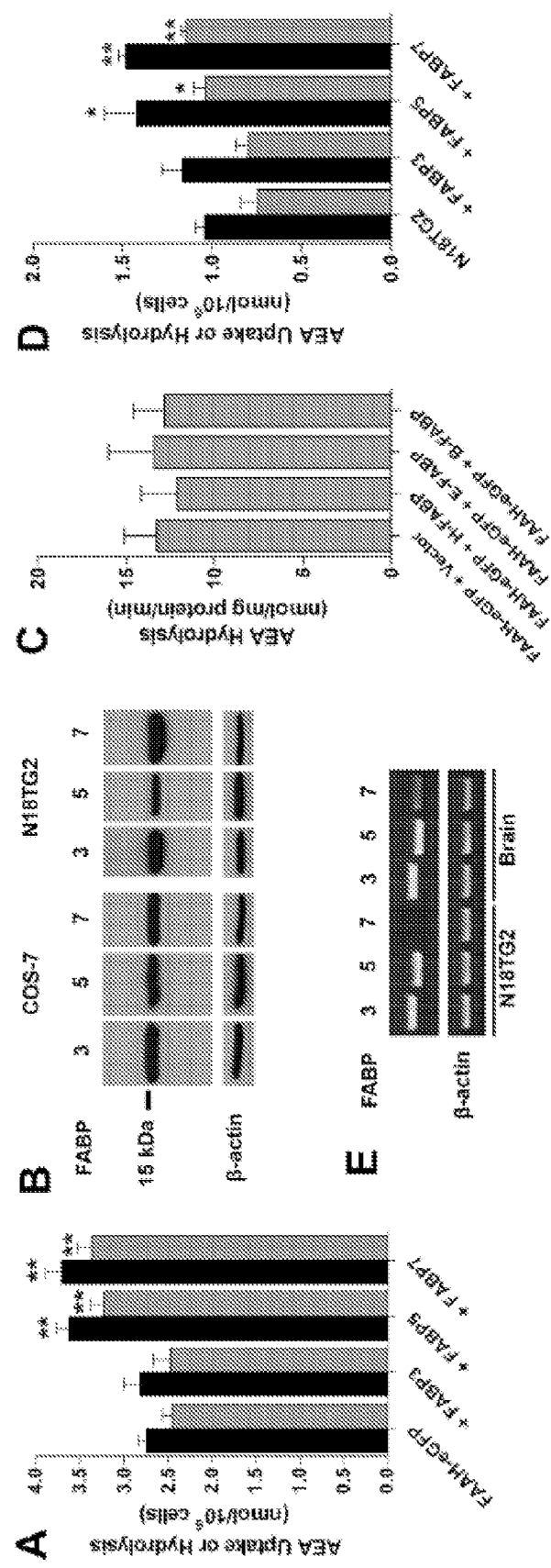
FIG. 3. Effect of FABP overexpression upon AEA uptake and hydrolysis. (a) Following a 10 minute incubation, [$^{14}$C] AEA uptake (black bars) and hydrolysis (grey bars) were elevated in COS-7-FAAH-eGFP cells following FABP5 or FABP7, but not FABP3, transfection. **, p<0.01 compared to vector transfected controls (n=3-5). (b) Western blot confirms the overexpression of FABP3, FABP5 or FABP7 in COS-7-FAAH-eGFP and N18TG2 transfected cells. (c) Overexpression of FABP3, FABP5, or FABP7 had no effect upon [$^{14}$C] AEA hydrolysis by COS-7-FAAH-eGFP homogenates (p>0.05). (d) [$^{14}$C]AEA uptake and hydrolysis by N18TG2 cells are enhanced following transfection with FABP5 and FABP7, but not FABP3. *, p<0.05 and **, p<0.01 compared to vector transfected controls (n=3-5). (e) RT-PCR analysis confirmed the endogenous expression of FABP3, FABP5, and FABP7 in brain and the expression of FABP3 and FABP5 in N18TG2 cells. B-actin serves as a control.

According to the present invention, there is further provided a method of identifying an agent for modulating the level of an endocannabinoid in a subject comprising testing the agent for its ability to modulate expression of an intracellular fatty acid binding protein. As set forth above, the expression of genes like those encoding fatty acid binding proteins, for example, may be detected and quantified according to methods commonly known in the art (see for example Sambrook et al., Molecular Cloning: A Laboratory Manual (Third Edition), Cold Spring Harbor Press, 2001). Examples of such methods include, or involve, quantitative reverse transcription-polymerase chain reaction (RT-PCR), real-time PCR, Northern blotting, Western blotting, immunohistochemistry, fluorescence activated cell sorting (FACS). Further, any of these approaches may be used in connection with an in vivo, ex vivo, or in vitro experimental setup. Examples of such methods also include the procedures and methods set forth, for example, in Examples 7 and 11, in FIG. 3, and elsewhere herein. Examples of GenBank accession numbers of individual FABPs are as follows: FABP 1—NM_001443; FABP 2—NM_000134; FABP 3—NM_004102; FABP 4—NM_001442; FABP 5—NM_001444; FABP 6—NM_001040442; FABP 7—NM_001446; FABP 8—NM_002677; FABP 9—NM_001080526.

Compounds can be further characterized in cellular assays that measure uptake and hydrolysis of endocannabinoids. For example, cell lines that express FAAH (e.g., N18TG2 mouse neuroblastoma, C6 mouse glioma) or cells transfected with FAAH can be preincubated with an inhibitor of an expressed FABP, and radiolabeled ligand (e.g., anandamide) added. (See, for example, Kaczocha et al. (2006) *J. Biol. Chem.* 281(14):9066-75). Optionally, FAAH activity may be determined to confirm that the agent is not an FAAH inhibitor. An assay of FAAH activity is provided by Glaser et al. (2003) *Proc. Natl. Acad. Sci. USA* 100:4269-4274.

According to the present invention, there is further provided a method of identifying an agent for treatment or amelioration of a neurological disorder comprising testing the agent for its ability to modulate the interaction of an endocannabinoid or FAA with an intracellular fatty acid binding protein. The interaction of an endocannabinoid or FAA with an intracellular fatty acid binding protein may be detected and quantified according to methods disclosed herein and other commonly known in the art. The physiological effect of the agent can be confirmed by a test or assay designed to evaluate endocannabinoid function in a subject. Examples of such methods are designed to evaluate movement, memory, mood, appetite, nociception, endocrine regulation, thermoregulation, sensory perception, and cognitive functions. Non-limiting examples include tail immersion (pain) (see Cravatt et al. (2001) Proc. Natl. Acad. Sci. USA 98:9371-6) and paw edema (inflammation) tests (see Wise et al. (2008) Neuropharmacology. 54:181-8).

The invention provides a kit useful for identifying a substance that inhibits binding of a ligand to an FABP expressed in the CNS. The kit comprises an FABP expressed in the CNS or a fatty acid amide-binding fragment or variant or derivative of the FABP, or a fusion protein comprising all or part of the FABP. In one embodiment, the kit includes a container or solid support for immobilizing the FABP. In an embodiment of the invention, the kit further comprises a ligand of the FABP which is used as a control or standard. In another embodiment of the invention, the FABP ligand in the kit is used in a competitive inhibition assay. In an embodiment of the invention, the ligand is a fatty acid amide, including, but not limited to a fatty acid amide that functions in the CNS. Such fatty acids include endocannabinoids, such as AEA or 2-AG or oleamide. In an embodiment of the invention, the ligand is the compound BMS309403 or the compound BMS480404. In a further embodiment, the kit includes a compound that inhibits binding of the ligand to the FABP. The inhibitor is particularly useful as control and/or for comparison to test substances. For example, when the ligand is an endocannabinoid (e.g., AEA), the binding inhibitor can be BMS309403. In an embodiment of the invention, the FABP and/or the ligand is conjugated to a reporter moiety, including, but not limited to, a radiolabel, a fluorescence label, and enzyme, or an immunologically detectable label. Typically, the kit will contain or be packaged with instructions for use as described herein.

Detailed descriptions of conventional methods, discussed herein such as those employed in the analysis of proteins, gene expression, light microscopy, bacterial culture, mammalian cell culture, and the like can be obtained from numerous publications such as Molecular Cloning: A Laboratory Manual (Cold Spring Harbor Laboratory Press. 1989), Current Protocols in Microbiology (Wiley InterScience), Current Protocols in Cell Biology (Wiley InterScience), and Current Protocols in Molecular Biology (Wiley InterScience). All references mentioned herein are incorporated by reference in their entirety.

EXAMPLES

The following examples further illustrate the invention, but should not be construed to limit the scope of the invention in any way.

Example 1

AEA Cellular Uptake is Rapid and Independent of FAAH's Subcellular Localization FAAH variants with distinct subcellular localizations were designed to explore putative trafficking mechanisms that may deliver AEA to intracellular FAAH. The rationale for this is as follows: if AEA primarily utilizes a directional mechanism for internalization (e.g., endocytosis), then AEA would be preferentially delivered to a specific target intracellular organelle. However, if AEA trafficking to FAAH involves a binding protein, its intracellular transport should be unaffected by the subcellular localization of FAAH.

COS-7 cells do not express FAAH and are therefore suitable for FAAH re-localization studies. Rat FAAH was fused to eGFP at its C-terminus (FIG. 1A). The N-terminal transmembrane (TM) helix of FAAH (residues 1-29) is dispensable for activity and was removed to allow the generation of other ΔTM-FAAH-eGFP fusion proteins. To localize FAAH to outer mitochondrial membranes or the Golgi apparatus, ΔTM-FAAH-eGFP was respectively fused at its N-terminus to the mitochondrial outer membrane targeting sequence from TOM20 or the Golgi resident protein Grasp65.

Stable cell-lines expressing these fusion proteins were generated and similar expression levels were confirmed by western blotting and activity assays (FIGS. 1B and C). Wild-type FAAH-eGFP (COS7-FAAH-eGFP) localized to the endoplasmic reticulum (ER), and in agreement with a previous study, mainly co-localized with an ER marker. TOM-ΔTM-FAAH-eGFP and GRASP-ΔTMFAAH-eGFP were confined to the mitochondria and Golgi apparatus, respectively (FIG. 1D). Protease protection experiments confirmed that all FAAH variants occupied the cytoplasmic face of membranes (FIG. 1E). Therefore, the cytosol represents the sole barrier for AEA delivery from the plasma membrane to FAAH.

AEA uptake and hydrolysis assays determined whether re-localization of FAAH to these organelles affected AEA inactivation. These assays tracked the cellular uptake of [$^{14}$C] AEA and its subsequent breakdown into [$^{14}$C]ethanolamine by FAAH. AEA uptake is coupled to its hydrolysis by FAAH, which maintains an outward/inward concentration gradient that increases AEA accumulation in the steady-state. Therefore, if AEA delivery to FAAH is reduced when FAAH expression is confined to the Golgi apparatus or mitochondria, the reduced hydrolysis of AEA will lower the AEA gradient and diminish its uptake. Conversely, enhanced AEA delivery to FAAH will result in increased hydrolysis of AEA and elevated accumulation.

Figure 2:
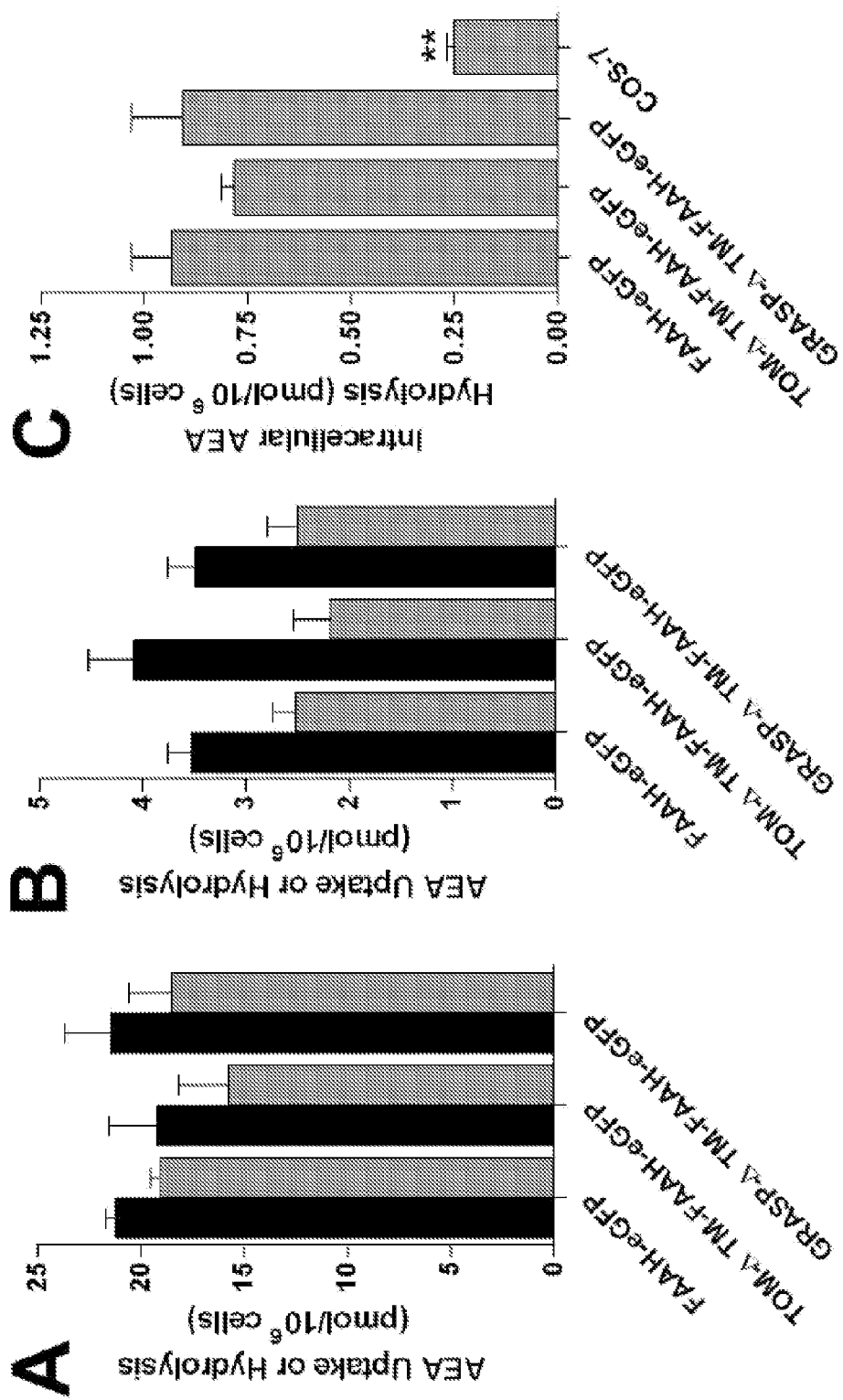
FIG. 2. Rapid inactivation of AEA in cells expressing spatially restricted FAAH variants. [$^{14}$C]AEA (100 nM) uptake (black bars) and hydrolysis (grey bars) were similar (P>0.05) in COS7-FAAH-eGFP, TOM-ΔTMFAAH-eGFP or GRASP-ΔTMFAAH-eGFP cells following (a) 5 min or (b) 10 sec incubations (n=3). (c) Similar levels of intracellular [$^{14}$C] AEA hydrolysis following a 3 sec incubation in COS7-FAAH-eGFP, TOM-ΔTMFAAH-eGFP or GRASP-ΔTM-FAAH-eGFP cells (p>0.05). Hydrolysis of [$^{14}$C]AEA in untransfected COS-7 cells was significantly lower than in FAAH-eGFP expressing controls. **, p<0.01 (n=3).

The uptake and hydrolysis of [$^{14}$C]AEA was similar between COS7-FAAH-eGFP, TOM-ΔTMFAAH-eGFP, and GRASP-ΔTMFAAH-eGFP cells at 5 min (FIG. 2A). Since this time point may allow for AEA to be taken up through one mechanism and subsequently redistributed intracellularly by others, these experiments were repeated using shorter time points. Similar to the results at 5 min, [$^{14}$C]AEA uptake and hydrolysis were unchanged between the three cell-lines at 10 sec (FIG. 2B). Identical results were obtained when the intracellular hydrolysis of [$^{14}$C]AEA following uptake was examined at 3 sec, with hydrolysis being similar in cells expressing all FAAH variants and significantly lower in cells lacking FAAH (FIG. 2C). These data suggest that AEA uptake and its subsequent delivery from the plasma membrane to FAAH occurs through an extremely rapid and organelle non-selective mechanism, which indicates intracellular transport by a carrier protein.

Example 2

The Uptake and Subsequent Hydrolysis of AEA are Enhanced by FABP5 and FABP7

The results presented thus far suggest that the transmembrane transport and subsequent intracellular delivery of AEA to FAAH is rapid. The hydrophobicity of AEA (estimated Log P value of 5.1) suggests that it is unlikely to diffuse efficiently from the plasma membrane to intracellular membranes containing FAAH unaided. Three members of the FABP family are expressed in brain, FABP3, FABP5 and FABP7. To determine whether these FABPs can potentiate AEA uptake and hydrolysis, COS7-FAAH-eGFP cells were transfected with each FABP and AEA uptake and metabolism analyzed. Overexpression of FABP5 and FABP7 but not FABP3 significantly enhanced the uptake of [$^{14}$C]AEA by 32% and 35%, respectively, compared to vector transfected cells (FIG. 3A). AEA hydrolysis was proportionally and significantly elevated. Western blotting confirmed that all three FABPs were successfully expressed in COS-7 cells (FIG. 3B). The hydrolysis of [$^{14}$C]AEA was similar in homogenates of vector transfected cells and in cells transfected with the FABPs (FIG. 3C), confirming that the overexpression of FABPs did not artifactually influence AEA uptake by modulating FAAH expression and/or activity.

To confirm that the function of FABPs as AEA carriers is independent of cell-type, these experiments were repeated in mouse neuroblastoma N18TG2 cells. These cells express $CB_1$ receptors, FAAH, and can take up and hydrolyze AEA. Similar to the results in COS-7 cells, overexpression of FABP5 and FABP7 significantly enhanced the uptake of [$^{14}$C]AEA by 36% and 42%, respectively (FIG. 3D). AEA hydrolysis was also proportionally and significantly elevated. Similar to COS-7 cells, western blotting confirmed that N18TG2 cells transfected with FABPs overexpressed these proteins (FIG. 3B). To confirm that these proteins constitute the endogenous repertoire of FABPs in N18TG2 cells, RT-PCR analysis was performed in N18TG2 cells and mouse brain as a control. As expected, and in accordance with previous data, FABP3, FABP5 and FABP7 were expressed in brain (FIG. 3E). Similarly, N18TG2 cells expressed FABP3 and FABP5, but not FABP7 (FIG. 3E). The lack of FABP7 expression in N18TG2 cells is consistent with the observation that FABP7 expression is confined to glial cells in the brain. Collectively, these data indicate that FABPs function as intracellular carriers for AEA, with FABP5 and FABP7 being more efficacious than FABP3.

Example 3

Inhibition of FABPs Reduces AEA Uptake and Hydrolysis

Figure 4:
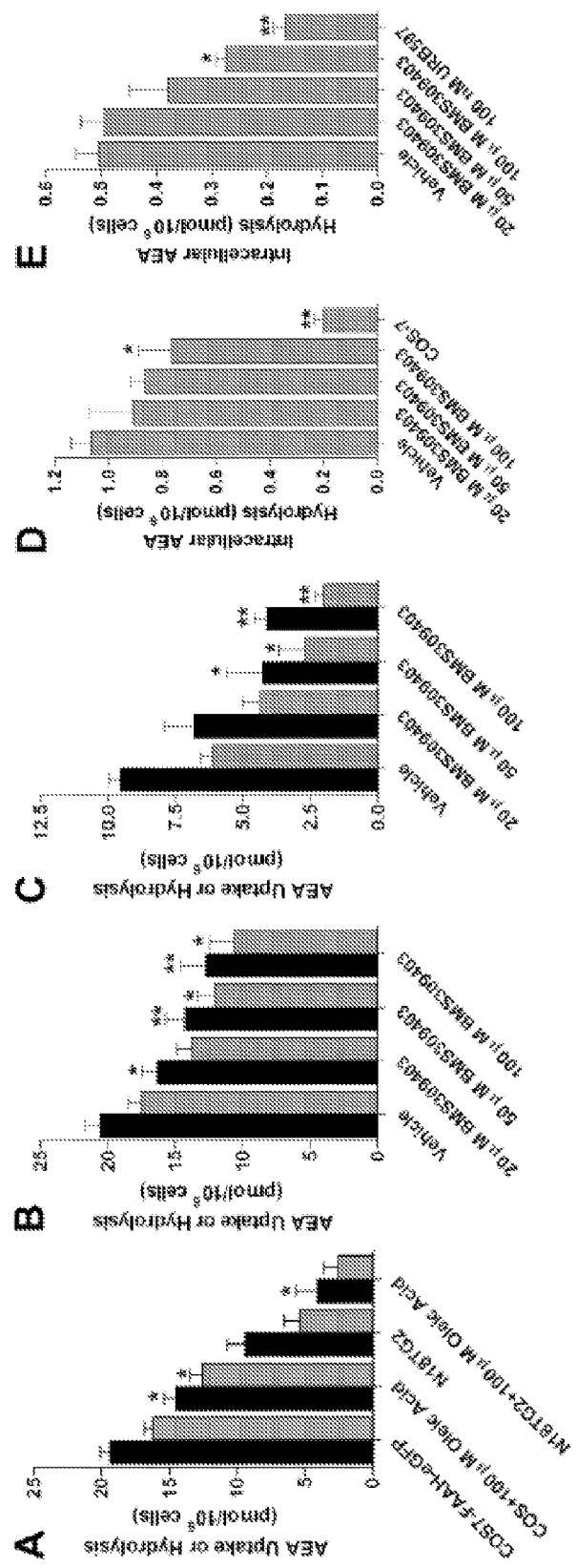
FIG. 4. Effect of FABP inhibition upon AEA internalization and hydrolysis by FAAH. (a) Treatment of COS-7-FAAH-eGFP and N18TG2 cells for 5 min with 100 μM oleic acid, a ligand for FABPs, significantly reduced [$^{14}$C]AEA uptake (black bars) and hydrolysis (grey bars). *, $p<0.05$ compared to vehicle-treated controls (n=3-5). (b,c) Treatment with 20-100 μM BMS309403, a selective competitive FABP inhibitor, significantly decreased [$^{14}$C]AEA uptake and metabolism by COS-7-FAAH-eGFP (b) or N18TG2 (c) cells. *, $p<0.05$ and **, $p<0.01$ compared to vehicle controls (n=3-5). (d,e) Increasing concentrations (20-100 μM) of BMS309403 reduced the hydrolysis of [$^{14}$C]AEA following cellular uptake by COS7-FAAH-eGFP (d) or N18TG2 (e) cells. *, $p<0.05$ and **, $p<0.01$ compared to vehicle treated controls (n=3-5).
Figure 5:
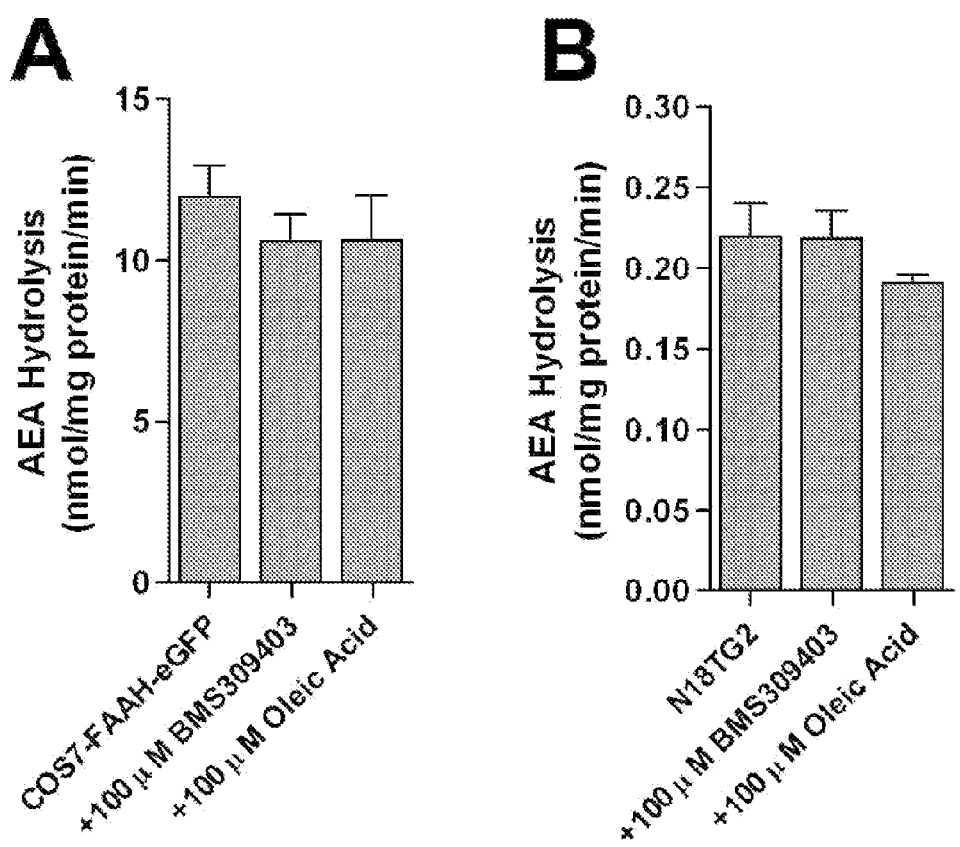
FIG. 5. Effect of BMS309403 and oleic acid upon FAAH activity in vitro. [$^{14}$C]AEA hydrolysis by (a) COS-7-FAAH-eGFP or (b) N18TG2 homogenates is not inhibited ($p>0.05$) by 100 μM oleic acid or BMS309403 (n=3).

Competitive FABP ligands/inhibitors were used to confirm the role of endogenous FABPs in cytosolic trafficking of AEA to FAAH. COS7-FAAH-eGFP and N18TG2 cells were incubated with the FABP ligand oleic acid (100 μM) and [$^{14}$C] AEA uptake measured following a 5 min incubation. Oleic acid reduced the uptake of [$^{14}$C]AEA in COS7-FAAH-eGFP and in N18TG2 cells by 25 and 53%, respectively (FIG. 4A). Since oleic acid lacks selectivity for FABPs, the experiments were repeated using the novel FABP inhibitor BMS309403. BMS309403 is a competitive inhibitor of FABPs with reported $IC_{50}$ values of 250 and 350 nM for FABP3 and FABP5, respectively. Treatment of COS7-FAAH-eGFP or N18TG2 cells with 20-100 μM BMS309403 resulted in a dose-dependent reduction in [$^{14}$C]AEA uptake with a maximal inhibition of 48 and 57%, respectively (FIGS. 4B and C). AEA hydrolysis was proportionally and significantly reduced. BMS309403 also reduced the intracellular hydrolysis of [$^{14}$C]AEA following uptake at 3 sec in both cell-types (FIGS. 4D and E) without affecting the levels of cell associated [$^{14}$C]AEA (data not shown). This confirms that BMS309403 attenuates the rapid intracellular trafficking of AEA to FAAH but not its delivery from the media to cells. The potency of BMS309403 was preserved in cells that were pre-treated with this inhibitor but subsequently incubated with [$^{14}$C]AEA alone (data not shown), confirming that its ability to reduce AEA uptake stems from the inhibition of a cellular target(s) rather than from artifactual competition for BSA binding in the incubation media. BMS309403 and oleic acid did not inhibit FAAH activity over the concentration range used in this study (FIG. 5), suggesting that their effects upon [$^{14}$C]AEA uptake and metabolism result from inhibition of intracellular transport rather than FAAH.

Results are expressed as means±SEM. Statistical significance was evaluated using two tailed unpaired t-tests against vector transfected or vehicle treated controls.

Example 4

RNA Interference-Mediated Knockdown of Fatty Acid Binding Proteins

The expression of fatty acid binding proteins (FABPs) is abrogated by RNA interference-mediated knockdown. Commercially available short hairpin RNAs (shRNA) targeting mouse and human FABP3, FABP5, or FABP7 are transiently or stably transfected into the neuronal cell lines N18TG2 (mouse neuroblastoma) and SH-SY5Y (human neuroblastoma). The degree of FABP knockdown is determined using RT-PCR and immunoblotting with antibodies against each FABP. Once knockdowns are established, changes in AEA uptake and hydrolysis are examined. (COS-7 cells may not be usable in this test since the genome of the African green monkey from which they are derived has not been sequenced.)

Example 5

Methods

Cell Culture and Generation of Stable Cell-Lines.
COS-7 and N18TG2 cells were grown in DMEM supplemented with 10% fetal bovine serum, 100 U/ml penicillin/streptomycin, 2 mM L-glutamine, and 1 mM sodium pyruvate in a humidified incubator containing 95% air and 5% $CO_2$. Transfections were carried out using Lipofectamine 2000 (Invitrogen, Carlsbad, Calif.) according to the manufacturer's instructions. For stable cell selection, forty eight hours after transfection cells were expanded in medium containing 750 μg/ml geneticin (Invitrogen, Carlsbad, Calif.). Four weeks later, stable cells were subjected to flow cytometry at the Flow Cytometry Core Facility in Stony Brook University and cells expressing identical levels of the indicated FAAH-eGFP fusion proteins were collected and expanded.

Cloning of Spatially Restricted FAAH Variants and FABPs.
Rat FAAH was PCR amplified and subcloned into the eGFP-N1 plasmid (Clonetech) using XhoI and KpnI and the following primers: forward 5'-TATA CTCGAGGCCACCATGGTGCTGAGCGAAGTGTG-3' (SEQ ID NO:13) and reverse 5'-TATAT GGTACCGACGATGGCTGCTTTTGAGG-3' (SEQ ID NO:14). Underlined nucleotides represent restriction sites while those in bold represent a Kozak consensus sequence. ΔTM-FAAH was subcloned into eGFP-N1 using XhoI and KpnI and the following primers: forward 5'-TATAT CTCGAGCGATGGACCGGGCGCCAG-3' (SEQ ID NO:15) and reverse 5'-GATATAT GGTACCGACGATGGCTGCTTTTGAGG-3' (SEQ ID NO:16). To localize FAAH to mitochondrial outer membranes, TOM20 (residues 1-33) was fused to the N-terminus of ΔTM-FAAH-eGFP using NheI and XhoI and the following primers: forward 5'-GATATAGCTAGCCACCATG GTGGGCCGGAACAGC-3' (SEQ ID NO:17) and reverse 5'-GATATACTCGAGGTTGGGGTCACTCCGCCTTT-3' (SEQ ID NO:18). To localize FAAH to the Golgi apparatus, Grasp65 was fused to the N-terminus of ΔTM-FAAH-eGFP using NheI and EcoRI. This ΔTM-FAAH-eGFP was fused to eGFP-N1 using EcoRI and KpnI rather than XhoI to facilitate subcloning of Grasp65. The following primers were used: forward 5'-GATATAGCTAGCGCCACCATGGGG CTAGGGGCAAGC-3' (SEQ ID NO:19) and reverse 5'-GATATAGAATTCCAGCCCAGGCTCTGGATCTGG-3' (SEQ ID NO:20). FABP3, FABP5, and FABP7 were cloned from mouse brain RNA using PCR and the following primers: FABP3 forward 5'-GATATAAAGCTTGCCACC ATGGCGGACGCCTTTGTC-3' (SEQ ID NO:21) and reverse 5'-GATATACTCGAGTCACGCCTCC TTCTCATAAGTC-3' (SEQ ID NO:22), FABP5 forward 5'-GATATAAAGCTTGCCACCATGGCCAGCCTTAAG GATC-3' (SEQ ID NO:23) and reverse 5'-GATATA CTCGAGTCATTGCACCTTCTCATAGAC-3' (SEQ ID NO:24), and FABP7 forward 5'-GATA GGTACCGCCACCATGGTAGATGCTTTCTGCGCAA-3' (SEQ ID NO:25) and reverse 5'-GATATA CTCGAGCTATGCCTTTTCATAACAGCGAAC-3' (SEQ ID NO:26). FABP3 and FABP5 were digested with HindIII and XhoI while FABP7 was cut with XhoI and KpnI and inserted into pcDNA4. All constructs were verified by DNA sequencing.

Immunolocalization of Fusion Proteins.

COS-7 cells stably expressing the indicated constructs were plated unto coverslips. To assess mitochondrial localization, the cells were treated with 175 nM Mitotracker Red CM-H$_2$XRos (Molecular Probes, Eugene, Oreg.) in DMEM+ 10% FBS for 25 min at 37° C., followed by fixation in 3% paraformaldehyde. For ER and Golgi apparatus co-localization studies, cells were processed essentially as described. Briefly, following fixation, cells were permeabilized with 0.2% Triton X-100 at 4° C. for 5 min and treated with rabbit anti-calreticulin antibodies (1:200) (Affinity Bioreagents, Golden, Colo.) or mouse anti-GM130 antibodies (1:100) (BD Transduction Labs, San Jose, Calif.) in 5% normal goat serum followed by donkey anti-rabbit or donkey anti-mouse IgG Alexa Fluor 594 (1:800) (Molecular Probes, Eugene, Oreg.). All images were acquired using a Zeiss LSM 510 META NLO Two-Photon Laser Scanning Microscope.

Western Blotting.

Ten (stable cell-lines) or fifty (FABP-transfected cells) micrograms of protein were run on a 10% SDS-PAGE gel. Following transfer to a nitrocellulose membrane at 100V for 25 min, the blots were blocked for one hour in 5% non-fat dry milk in PBS Tween (PBST). The blots were probed with rabbit anti-eGFP (1:2000) (Molecular Probes, Eugene, Oreg.), mouse anti-13 actin (1:10000-1:100000) or mouse anti-FABP3 (1:100) (Abcam, Cambridge, Mass.), rabbit anti-FABP5 (1:100) or rabbit anti-FABP7 (1:100) (Santa Cruz Biotechnology, Santa Cruz, Calif.) antibodies for 1 hour with shaking. The blots were rinsed three times with PBST followed by incubation with goat anti-mouse or goat anti-rabbit IgG HRP-conjugated antibodies (Molecular Probes, Eugene, Oreg.) for 1 hour. The blots were rinsed three times with PBST, developed using the Immun-star HRP substrate (Bio-Rad, Hercules, Calif.) and exposed to film.

Proteinase K Protection Analysis.

COS-7 cells were homogenized by passage through a 26 gauge needle in buffer A (10 mM HEPES-NaOH pH 7.5 containing 1 mM EDTA, 1.5 mM MgCl$_2$, 10 mM KCl and 250 mM sucrose). Unbroken cells and nuclei were pelleted by centrifugation at 1000 g for 10 min and the resulting supernatant was subjected to centrifugation at 100,000 g for 60 min at 4° C. The pellet containing membranes was resuspended in buffer B (50 mM Tris pH 8, 3 mM CaCl$_2$, 1.5 mM MgCl$_2$, 10 mM KCl, 100 mM NaCl, 250 mM sucrose) and treated with 500 µg/ml proteinase K for 30 min at 37° C. in the presence or absence of 1% Triton X-100, or left untreated. The reactions were quenched by the addition of 20 mM PMSF. Control experiments using Proteinase K pre-treated with PMSF revealed near complete inhibition of the enzyme (data not shown). The samples were separated by SDS-PAGE and visualized by immunoblotting with anti-eGFP or anti-calreticulin (1:2000) (Affinity Bioreagents, Golden, Colo.) antibodies.

FAAH Enzyme Assays.

FAAH activity assays were performed as previously described. Briefly, cell homogenates were incubated with 100 µM AEA+0.1 µCi [$^{14}$C]AEA in Tris-HCl (pH 9) containing 0.1% BSA. For activity analysis, time and total protein were adjusted to maintain substrate conversion at approximately 10%. For inhibitor studies, 50 µg of COS-7 or 100 µg N18TG2 homogenates were pre-treated with 100 µM oleic acid, BMS309403, or vehicle (DMSO) control for 15 min followed by incubation with [$^{14}$C]AEA (100 µM) for 1 or 30 min, respectively. Reactions were stopped by the addition of two volumes of 1:1 chloroform:methanol and the phases separated by centrifugation. The methanol phase (containing [$^{14}$C]ethanolamine) was sampled and quantified using a Beckman LS 6500 scintillation counter.

Determination and Inhibition of AEA Cellular Uptake and Hydrolysis.

Cells were plated at ~90% confluency in 35 mm dishes, washed twice in DMEM and preincubated with the desired pharmacological compounds or vehicle controls (EtOH or DMSO). The cells were washed twice in DMEM and subsequently incubated for 5 min, 10 or 3 sec, with 750 µl [$^{14}$C] AEA (100 nM) that was pre-equilibrated for 75 min in medium containing 0.15% BSA. The equilibration step is necessary to avoid uneven distribution of the radiotracer and to ensure that it is stable in solution pre-bound to BSA. Less than 1% of AEA was hydrolyzed during this pre-equilibration step (data not shown). Following the incubation, 750 µl of ice-cold DMEM+0.15% BSA was added to the plates, the media separated from cells, which were then washed with DMEM+0.15% BSA to remove non-specifically bound AEA. The cells were scraped three times with 400 µl of ice-cold 2 mM EDTA in PBS and chloroform:methanol (1:1) added to the media and cells and the phases separated by centrifugation. The resulting aqueous (containing [$^{14}$C]ethanolamine) and organic (containing intact [$^{14}$C]AEA) phases were counted by liquid scintillation counting. [$^{14}$C]AEA uptake was determined by summing the production of [$^{14}$C]ethanolamine in the media and cells with intact cellular [$^{14}$C]AEA. Hydrolysis of [$^{14}$C]AEA was quantified by production of [$^{14}$C]ethanolamine in the media and cells. Blanks consisting of either untransfected COS-7 cells or N18TG2 cells treated with 100 nM of the FAAH inhibitor URB597 were subtracted from all conditions.

RT-PCR Analysis of Endogenous FABP Expression.

One microgram of RNA extracted from mouse brain or N18TG2 cells using the RNeasy mini kit (Qiagen, Valencia, Calif.) was subjected to cDNA synthesis using the Superscript III first strand synthesis kit (Invitrogen, Carlsbad, Calif.). The resulting cDNAs were subjected to PCR using primers specific for FABP3, FABP5, FABP7, or β-actin. The following primers were used. For FABP3, forward 5'-CATC-GAGAAGAACGGGGATA-3' (SEQ ID NO:27) and reverse 5'-TGCCATGAGTGAGAGTCAGG-3' (SEQ ID NO:28); FABP5 forward 5'-CAAAACCGAGAGCACAGTGA-3' (SEQ ID NO:29) and reverse 5'-CACGATCATCTTC-CCATCCT-3' (SEQ ID NO:30); FABP7 forward 5'-AGTGG-GAAACGTGACCAAAC-3' (SEQ ID NO:31) and 5'-TTTCTTTGCCATCCCACTTC-3' (SEQ ID NO:32); and β-actin forward 5'-AGATGACCCAGATCATGTTTGA-3' (SEQ ID NO:33) and reverse 5'-CACAGCTTCTCCTTAAT-GTCA-3' (SEQ ID NO:34). The following cycling conditions were used: denaturation at 94° C. for 30 sec, annealing at 58° C. for 30 sec, and extension at 72° C. for 30 sec for a total of 30 cycles. The resulting products were visualized on an agarose gel.

We claim:

1. A method of increasing the level of an endocannabinoid in a subject in need thereof comprising administering to the subject an effective amount of an agent that inhibits the binding of the endocannabinoid with fatty acid binding protein 5 (FABP5) in the subject.

2. The method of claim 1, wherein the level of the endocannabinoid is increased in the CNS.

3. The method of claim 1, wherein the endocannabinoid is 2 arachidonoylglycerol (2-AG).

4. The method of claim 1, wherein the endocannabinoid is anandamide (AEA).

5. The method of claim 1, wherein the increase in the level of the endocannabinoid treats or ameliorates a neurological disorder.

6. The method of claim 1, wherein the agent is BMS-309403 or BMS-480404.

7. The method of claim 1, wherein the subject is a human.

8. The method of claim 5, wherein the neurological disorder affects at least one of movement, memory, mood, appetite, nociception, endocrine regulation, thermoregulation, sensory perception, and cognitive functions.

9. The method of claim 5, wherein the neurological disorder is drug addiction, depression, compulsive behavior, neuropathic pain, or a movement disorder.

10. A method of increasing the level of an endocannabinoid in a subject in need thereof comprising administering to the subject an effective amount of an agent that inhibits the binding of the endocannabinoid with fatty acid binding protein 7 (FABP7) in the subject.

11. The method of claim 10, wherein the level of the endocannabinoid is increased in the CNS.

12. The method of claim 10, wherein the endocannabinoid is 2-arachidonoylglycerol (2-AG).

13. The method of claim 10, wherein the endocannabinoid is anandamide (AEA).

14. The method of claim 10, wherein the increase in the level of the endocannabinoid treats or ameliorates a neurological disorder.

15. The method of claim 10, wherein the agent is BMS-309403 or BMS-480404.

16. The method of claim 14, wherein the neurological disorder affects at least one of movement, memory, mood, appetite, nociception, endocrine regulation, thermoregulation, sensory perception, and cognitive functions.

17. The method of claim 14, wherein the neurological disorder is drug addiction, depression, compulsive behavior, neuropathic pain, or a movement disorder.

18. The method of claim 14, wherein the subject is a human.

* * * * *

```
                            SEQUENCE LISTING

<160> NUMBER OF SEQ ID NOS: 34

<210> SEQ ID NO 1
<211> LENGTH: 29
<212> TYPE: RNA
<213> ORGANISM: Artificial Sequence
<220> FEATURE:
<223> OTHER INFORMATION: Synthetic RNA

<400> SEQUENCE: 1
accuggaagc uaguggacag caagaauuu                                      29

<210> SEQ ID NO 2
<211> LENGTH: 29
<212> TYPE: RNA
<213> ORGANISM: Artificial Sequence
<220> FEATURE:
<223> OTHER INFORMATION: Synthetic RNA

<400> SEQUENCE: 2
agcaugacca agccuaccac aaucaucga                                      29

<210> SEQ ID NO 3
<211> LENGTH: 29
<212> TYPE: RNA
<213> ORGANISM: Artificial Sequence
<220> FEATURE:
<223> OTHER INFORMATION: Synthetic RNA

<400> SEQUENCE: 3
agcaccuuca agaacacaga gaucagcuu                                      29

<210> SEQ ID NO 4
<211> LENGTH: 29
<212> TYPE: RNA
<213> ORGANISM: Artificial Sequence
<220> FEATURE:
<223> OTHER INFORMATION: Synthetic RNA

<400> SEQUENCE: 4
gcagaugaca ggaaggucaa guccauugu                                      29

<210> SEQ ID NO 5
<211> LENGTH: 29
<212> TYPE: RNA
<213> ORGANISM: Artificial Sequence
<220> FEATURE:
<223> OTHER INFORMATION: Synthetic RNA

<400> SEQUENCE: 5
gccacaguuc agcagcugga aggaagaug                                      29

<210> SEQ ID NO 6
<211> LENGTH: 29
<212> TYPE: RNA
```

```
<213> ORGANISM: Artificial Sequence
<220> FEATURE:
<223> OTHER INFORMATION: Synthetic RNA

<400> SEQUENCE: 6
cugguggaca gcaaaggcuu ugaugaaua                                              29

<210> SEQ ID NO 7
<211> LENGTH: 29
<212> TYPE: RNA
<213> ORGANISM: Artificial Sequence
<220> FEATURE:
<223> OTHER INFORMATION: Synthetic RNA

<400> SEQUENCE: 7
aguuugaaga aaccacagcu gauggcaga                                              29

<210> SEQ ID NO 8
<211> LENGTH: 29
<212> TYPE: RNA
<213> ORGANISM: Artificial Sequence
<220> FEATURE:
<223> OTHER INFORMATION: Synthetic RNA

<400> SEQUENCE: 8
gaacaauguc accuguacuc ggaucuaug                                              29

<210> SEQ ID NO 9
<211> LENGTH: 29
<212> TYPE: RNA
<213> ORGANISM: Artificial Sequence
<220> FEATURE:
<223> OTHER INFORMATION: Synthetic RNA

<400> SEQUENCE: 9
ugguggaggc uuucugugcu accuggaag                                              29

<210> SEQ ID NO 10
<211> LENGTH: 29
<212> TYPE: RNA
<213> ORGANISM: Artificial Sequence
<220> FEATURE:
<223> OTHER INFORMATION: Synthetic RNA

<400> SEQUENCE: 10
aggacucuca gcacauucaa gaacacgga                                              29

<210> SEQ ID NO 11
<211> LENGTH: 29
<212> TYPE: RNA
<213> ORGANISM: Artificial Sequence
<220> FEATURE:
<223> OTHER INFORMATION: Synthetic RNA

<400> SEQUENCE: 11
aacuguaagu cuguuguuag ccuggaugg                                              29

<210> SEQ ID NO 12
<211> LENGTH: 29
<212> TYPE: RNA
<213> ORGANISM: Artificial Sequence
<220> FEATURE:
<223> OTHER INFORMATION: synthetic RNA

<400> SEQUENCE: 12
ugguugcugu ucgccacuau gagaaggca                                              29
```

<210> SEQ ID NO 13
<211> LENGTH: 36
<212> TYPE: DNA
<213> ORGANISM: Artificial Sequence
<220> FEATURE:
<223> OTHER INFORMATION: Synthetic primer

<400> SEQUENCE: 13
tatactcgag gccaccatgg tgctgagcga agtgtg                                  36

<210> SEQ ID NO 14
<211> LENGTH: 31
<212> TYPE: DNA
<213> ORGANISM: Artificial Sequence
<220> FEATURE:
<223> OTHER INFORMATION: Synthetic primer

<400> SEQUENCE: 14
tatatggtac cgacgatggc tgcttttgag g                                       31

<210> SEQ ID NO 15
<211> LENGTH: 29
<212> TYPE: DNA
<213> ORGANISM: Artificial Sequence
<220> FEATURE:
<223> OTHER INFORMATION: Synthetic primer

<400> SEQUENCE: 15
tatatctcga gcgatggacc gggcgccag                                          29

<210> SEQ ID NO 16
<211> LENGTH: 33
<212> TYPE: DNA
<213> ORGANISM: Artificial Sequence
<220> FEATURE:
<223> OTHER INFORMATION: Synthetic primer

<400> SEQUENCE: 16
gatatatggt accgacgatg gctgcttttg agg                                     33

<210> SEQ ID NO 17
<211> LENGTH: 36
<212> TYPE: DNA
<213> ORGANISM: Artificial Sequence
<220> FEATURE:
<223> OTHER INFORMATION: Synthetic primer

<400> SEQUENCE: 17
gatatagcta gcgccaccat ggtgggccgg aacagc                                  36

<210> SEQ ID NO 18
<211> LENGTH: 32
<212> TYPE: DNA
<213> ORGANISM: Artificial Sequence
<220> FEATURE:
<223> OTHER INFORMATION: Synthetic primer

<400> SEQUENCE: 18
gatatactcg aggttggggt cactccgcct tt                                      32

<210> SEQ ID NO 19
<211> LENGTH: 36
<212> TYPE: DNA
<213> ORGANISM: Artificial Sequence
<220> FEATURE:

<223> OTHER INFORMATION: Synthetic primer

<400> SEQUENCE: 19
gatatagcta gcgccaccat ggggctaggg gcaagc                                  36

<210> SEQ ID NO 20
<211> LENGTH: 33
<212> TYPE: DNA
<213> ORGANISM: Unknown
<220> FEATURE:
<223> OTHER INFORMATION: Synthetic primer

<400> SEQUENCE: 20
gatatagaat tccagcccag gctctggatc tgg                                     33

<210> SEQ ID NO 21
<211> LENGTH: 36
<212> TYPE: DNA
<213> ORGANISM: Artificial Sequence
<220> FEATURE:
<223> OTHER INFORMATION: Synthetic primer

<400> SEQUENCE: 21
gatataaagc ttgccaccat ggcggacgcc tttgtc                                  36

<210> SEQ ID NO 22
<211> LENGTH: 34
<212> TYPE: DNA
<213> ORGANISM: Artificial Sequence
<220> FEATURE:
<223> OTHER INFORMATION: Synthetic primer

<400> SEQUENCE: 22
gatatactcg agtcacgcct ccttctcata agtc                                    34

<210> SEQ ID NO 23
<211> LENGTH: 37
<212> TYPE: DNA
<213> ORGANISM: Artificial Sequence
<220> FEATURE:
<223> OTHER INFORMATION: Synthetic primer

<400> SEQUENCE: 23
gatataaagc ttgccaccat ggccagcctt aaggatc                                 37

<210> SEQ ID NO 24
<211> LENGTH: 33
<212> TYPE: DNA
<213> ORGANISM: Artificial Sequence
<220> FEATURE:
<223> OTHER INFORMATION: Synthetic primer

<400> SEQUENCE: 24
gatatactcg agtcattgca ccttctcata gac                                     33

<210> SEQ ID NO 25
<211> LENGTH: 38
<212> TYPE: DNA
<213> ORGANISM: Artificial Sequence
<220> FEATURE:
<223> OTHER INFORMATION: Synthetic primer

<400> SEQUENCE: 25
gataggtacc gccaccatgg tagatgcttt ctgcgcaa                                38

```
<210> SEQ ID NO 26
<211> LENGTH: 36
<212> TYPE: DNA
<213> ORGANISM: Unknown
<220> FEATURE:
<223> OTHER INFORMATION: Synthetic primer

<400> SEQUENCE: 26
gatatactcg agctatgcct tttcataaca gcgaac                              36

<210> SEQ ID NO 27
<211> LENGTH: 20
<212> TYPE: DNA
<213> ORGANISM: Artificial Sequence
<220> FEATURE:
<223> OTHER INFORMATION: Synthetic Primer

<400> SEQUENCE: 27
catcgagaag aacggggata                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
tgccatgagt gagagtcagg                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
caaaaccgag agcacagtga                                                20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
cacgatcatc ttcccatcct                                                20

<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31
agtgggaaac gtgaccaaac                                                20

<210> SEQ ID NO 32
<211> LENGTH: 20
<212> TYPE: DNA
<213> ORGANISM: Unknown
<220> FEATURE:
<223> OTHER INFORMATION: Synthetic primer
```

```
<400> SEQUENCE: 32
tttctttgcc atcccacttc                                                   20

<210> SEQ ID NO 33
<211> LENGTH: 22
<212> TYPE: DNA
<213> ORGANISM: Unknown
<220> FEATURE:
<223> OTHER INFORMATION: Synthetic primer

<400> SEQUENCE: 33
agatgaccca gatcatgttt ga                                                22

<210> SEQ ID NO 34
<211> LENGTH: 21
<212> TYPE: DNA
<213> ORGANISM: Artificial Sequence
<220> FEATURE:
<223> OTHER INFORMATION: Synthetic primer

<400> SEQUENCE: 34
cacagcttct ccttaatgtc a                                                 21
```